(12) United States Patent
Nobles et al.

(10) Patent No.: US 10,828,022 B2
(45) Date of Patent: Nov. 10, 2020

(54) SUTURING DEVICES AND METHODS FOR SUTURING AN ANATOMIC STRUCTURE

(71) Applicant: Med-Venture Investments, LLC, Fountain Valley, CA (US)

(72) Inventors: Anthony A. Nobles, Fountain Valley, CA (US); Benjamin G. Brosch, Mission Viejo, CA (US)

(73) Assignee: Med-Venture Investments, LLC, Fountain Valley, CA (US)

( * ) Notice: Subject to any disclaimer, the term of this patent is extended or adjusted under 35 U.S.C. 154(b) by 697 days.

(21) Appl. No.: 14/901,831

(22) PCT Filed: Jun. 26, 2014

(86) PCT No.: PCT/US2014/044429
§ 371 (c)(1),
(2) Date: Dec. 29, 2015

(87) PCT Pub. No.: WO2015/002815
PCT Pub. Date: Jan. 8, 2015

(65) Prior Publication Data
US 2016/0151064 A1 Jun. 2, 2016

Related U.S. Application Data

(60) Provisional application No. 61/842,304, filed on Jul. 2, 2013.

(51) Int. Cl.
*A61B 17/04* (2006.01)
*A61B 17/06* (2006.01)
(52) U.S. Cl.
CPC ...... *A61B 17/0469* (2013.01); *A61B 17/0482* (2013.01); *A61B 2017/0472* (2013.01); *A61B 2017/06042* (2013.01)

(58) Field of Classification Search
CPC . A61B 17/0057; A61B 17/04; A61B 17/0469; A61B 17/0482; A61B 17/0483;
(Continued)

(56) References Cited

U.S. PATENT DOCUMENTS 118,683 A 9/1871 Bruce
1,064,307 A 6/1913 Fleming
(Continued)

FOREIGN PATENT DOCUMENTS

AU 2006251579 11/2006
CN 101495049 12/2010
(Continued)

OTHER PUBLICATIONS

Advances in Vascular Surgery, by John S. Najarian, M.D. and John P. Delaney, M.D., copyright 1983 by Year Book Publishers, Inc. at pp. 94,95,96, and 224.
(Continued)

*Primary Examiner* — Todd J Scherbel
(74) *Attorney, Agent, or Firm* — Knobbe, Martens, Olson & Bear, LLP

(57) ABSTRACT

Suturing devices and systems used to apply sutures and/or to close openings at, within, or into a biological structure. The suturing device can comprise an elongate member having a proximal end, a distal end, one or more distal arms, one or more proximal extensions, and one or more needles. A sheath may be used with the device to maintain or substantially maintain haemostasis while the device is used and while a procedure is performed in the biological structure.

26 Claims, 18 Drawing Sheets

(58) Field of Classification Search
CPC .......... A61B 2017/00575; A61B 2017/00663;
A61B 2017/0472; A61B 2017/0477
See application file for complete search history.

(56) References Cited

U.S. PATENT DOCUMENTS

| | | |
|---|---|---|
| 1,822,330 A | 9/1931 | Ainslie |
| 1,989,919 A | 2/1935 | Everitt |
| 2,348,218 A | 5/1944 | Karle |
| 2,473,742 A | 6/1949 | Auzin |
| 2,548,602 A | 4/1951 | Greenburg |
| 2,637,290 A | 5/1953 | Sigoda |
| 2,849,002 A | 8/1958 | Oddo |
| 2,945,460 A | 7/1960 | Kagiyama |
| 3,241,554 A | 3/1966 | Coanda |
| 3,292,627 A | 12/1966 | Harautuneian |
| 3,394,705 A | 7/1968 | Abramson |
| 3,664,345 A | 5/1972 | Dabbs et al. |
| 3,665,926 A | 5/1972 | Flores |
| 3,774,596 A | 11/1973 | Cook |
| 3,828,790 A | 8/1974 | Curtiss et al. |
| 3,831,587 A | 8/1974 | Boyd |
| 3,842,840 A | 10/1974 | Schweizer |
| 3,877,434 A | 4/1975 | Samuels |
| 3,882,852 A | 5/1975 | Sinnreich |
| 3,882,855 A | 5/1975 | Schulte et al. |
| 3,888,117 A | 6/1975 | Lewis |
| 3,903,893 A | 9/1975 | Scheer |
| 3,946,740 A | 3/1976 | Bassett |
| 3,946,741 A | 3/1976 | Adair |
| 3,952,742 A | 4/1976 | Taylor |
| 3,976,079 A | 8/1976 | Samuels |
| 4,052,980 A | 10/1977 | Grams et al. |
| RE29,703 E | 7/1978 | Fatt |
| 4,107,953 A | 8/1978 | Casillo |
| 4,119,100 A | 10/1978 | Rickett |
| 4,164,225 A | 8/1979 | Johnson et al. |
| 4,230,119 A | 10/1980 | Blum |
| 4,291,698 A | 9/1981 | Fuchs et al. |
| 4,299,237 A | 11/1981 | Foti |
| 4,307,722 A | 12/1981 | Evans |
| 4,345,601 A | 8/1982 | Fukuda |
| 4,351,342 A | 9/1982 | Wiita et al. |
| 4,417,532 A | 11/1983 | Yasukata |
| 4,423,725 A | 1/1984 | Baran et al. |
| 4,447,227 A | 5/1984 | Kotsanis |
| 4,457,300 A | 7/1984 | Budde |
| 4,484,580 A | 11/1984 | Nomoto et al. |
| 4,512,338 A | 4/1985 | Balko et al. |
| 4,546,759 A | 10/1985 | Solar |
| 4,553,543 A | 11/1985 | Amarasinghe |
| 4,573,966 A | 3/1986 | Weikl et al. |
| 4,589,868 A | 5/1986 | Dretler |
| 4,610,662 A | 9/1986 | Weikl et al. |
| 4,617,738 A | 10/1986 | Kopacz |
| 4,662,068 A | 5/1987 | Polonsky |
| 4,664,114 A | 5/1987 | Ghodsian |
| 4,734,094 A | 3/1988 | Jacob et al. |
| 4,744,364 A | 5/1988 | Kensey |
| 4,750,492 A | 6/1988 | Jacobs |
| 4,771,776 A | 9/1988 | Powell et al. |
| 4,774,091 A | 9/1988 | Yamahira et al. |
| 4,794,928 A | 1/1989 | Kletschka |
| 4,795,427 A | 1/1989 | Helzel |
| 4,796,629 A | 1/1989 | Grayzel |
| 4,824,436 A | 4/1989 | Wolinsky |
| 4,827,931 A | 5/1989 | Longmore |
| 4,841,888 A | 6/1989 | Mills et al. |
| 4,861,330 A | 8/1989 | Voss |
| 4,898,168 A | 2/1990 | Yule |
| 4,923,461 A | 5/1990 | Caspari et al. |
| 4,926,860 A | 5/1990 | Stice et al. |
| 4,932,956 A | 6/1990 | Reddy et al. |
| 4,935,027 A | 6/1990 | Yoon |
| 4,954,126 A | 9/1990 | Wallsten |
| 4,957,498 A | 9/1990 | Caspari et al. |
| 4,972,845 A | 11/1990 | Iversen et al. |
| 4,981,149 A | 1/1991 | Yoon et al. |
| 4,983,116 A | 1/1991 | Koga |
| 4,984,564 A | 1/1991 | Yuen |
| 4,994,070 A | 2/1991 | Waters |
| 5,002,531 A | 3/1991 | Bonzel |
| 5,021,059 A | 6/1991 | Kensey et al. |
| 5,037,433 A | 8/1991 | Wilk et al. |
| 5,057,114 A | 10/1991 | Wittich et al. |
| 5,059,201 A | 10/1991 | Asnis |
| 5,065,772 A | 11/1991 | Cox, Jr. |
| 5,074,871 A | 12/1991 | Groshong |
| 5,078,743 A | 1/1992 | Mikalov et al. |
| 5,090,958 A | 2/1992 | Sahota |
| 5,100,418 A | 3/1992 | Yoon et al. |
| 5,104,394 A | 4/1992 | Knoepfler |
| 5,106,363 A | 4/1992 | Nobuyoshi |
| 5,108,416 A | 4/1992 | Ryan et al. |
| 5,108,419 A | 4/1992 | Reger et al. |
| 5,116,305 A | 5/1992 | Milder et al. |
| 5,122,122 A | 6/1992 | Allgood |
| 5,129,883 A | 7/1992 | Black |
| 5,133,724 A | 7/1992 | Wilson et al. |
| 5,135,484 A | 8/1992 | Wright |
| 5,160,339 A | 11/1992 | Chen et al. |
| 5,163,906 A | 11/1992 | Ahmadi |
| 5,167,223 A | 12/1992 | Koros et al. |
| 5,171,251 A | 12/1992 | Bregen et al. |
| 5,176,691 A | 1/1993 | Pierce |
| 5,192,301 A | 3/1993 | Kamiya et al. |
| 5,222,508 A | 6/1993 | Contarini |
| 5,222,941 A | 6/1993 | Don Michael |
| 5,222,974 A | 6/1993 | Kensey et al. |
| 5,224,948 A | 7/1993 | Abe et al. |
| 5,236,443 A | 8/1993 | Sontag |
| 5,242,459 A | 9/1993 | Buelna |
| 5,281,234 A | 1/1994 | Wilk et al. |
| 5,281,237 A | 1/1994 | Gimpelson |
| 5,282,827 A | 2/1994 | Kensey et al. |
| 5,286,259 A | 2/1994 | Ganguly et al. |
| 5,290,249 A | 3/1994 | Foster et al. |
| 5,300,106 A | 4/1994 | Dahl et al. |
| 5,304,184 A | 4/1994 | Hathaway et al. |
| 5,308,323 A | 5/1994 | Sogawa et al. |
| 5,312,344 A | 5/1994 | Grinfeld |
| 5,314,409 A | 5/1994 | Sarosiek et al. |
| 5,320,604 A | 6/1994 | Walker et al. |
| 5,320,632 A | 6/1994 | Heidmueller |
| 5,330,446 A | 7/1994 | Weldon et al. |
| 5,330,497 A | 7/1994 | Freitas et al. |
| 5,331,975 A | 7/1994 | Bonutti |
| 5,336,229 A | 8/1994 | Noda |
| 5,336,231 A | 8/1994 | Adair |
| 5,337,736 A | 8/1994 | Reddy |
| 5,339,801 A | 8/1994 | Poloyko |
| 5,342,306 A | 8/1994 | Don Michael |
| 5,342,385 A | 8/1994 | Norelli et al. |
| 5,342,393 A | 8/1994 | Stack |
| 5,350,399 A | 9/1994 | Erlebacher et al. |
| 5,356,382 A | 10/1994 | Picha et al. |
| 5,364,407 A | 11/1994 | Poll |
| 5,364,408 A | 11/1994 | Gordon |
| 5,368,601 A | 11/1994 | Sauer et al. |
| 5,370,618 A | 12/1994 | Leonhardt |
| 5,370,685 A | 12/1994 | Stevens |
| 5,374,275 A | 12/1994 | Bradley et al. |
| 5,380,284 A | 1/1995 | Don Michael |
| 5,382,261 A | 1/1995 | Palmaz |
| 5,383,854 A | 1/1995 | Safar et al. |
| 5,383,896 A | 1/1995 | Gershony et al. |
| 5,383,897 A | 1/1995 | Wholey |
| 5,383,905 A | 1/1995 | Golds et al. |
| 5,389,103 A | 2/1995 | Melzer et al. |
| 5,391,147 A | 2/1995 | Imran et al. |
| 5,391,174 A | 2/1995 | Weston |
| 2,738,790 A | 3/1995 | Todt, Sr. et al. |
| 5,395,383 A | 3/1995 | Adams et al. |
| 5,397,325 A | 3/1995 | Badia et al. |

(56) References Cited

U.S. PATENT DOCUMENTS

| | | |
|---|---|---|
| 5,403,329 A | 4/1995 | Hinchcliffe |
| 5,403,331 A | 4/1995 | Chesterfield et al. |
| 5,403,341 A | 4/1995 | Solar |
| 5,405,322 A | 4/1995 | Lennox et al. |
| 5,405,354 A | 4/1995 | Sarrett |
| 5,417,699 A | 5/1995 | Klein et al. |
| 5,417,700 A | 5/1995 | Egan |
| 5,423,777 A | 6/1995 | Tajiri et al. |
| 5,423,837 A | 6/1995 | Mericle et al. |
| 5,425,708 A | 6/1995 | Nasu |
| 5,425,737 A | 6/1995 | Burbank et al. |
| 5,425,744 A | 6/1995 | Fagan et al. |
| 5,429,118 A | 7/1995 | Cole et al. |
| 5,431,666 A | 7/1995 | Sauer et al. |
| 5,439,470 A | 8/1995 | Li |
| 5,445,167 A | 8/1995 | Yoon et al. |
| 5,447,515 A | 9/1995 | Robicsek |
| 5,452,513 A | 9/1995 | Zinnbauer et al. |
| 5,454,823 A | 10/1995 | Richardson et al. |
| 5,458,574 A | 10/1995 | Machold et al. |
| 5,458,609 A | 10/1995 | Gordon et al. |
| 5,462,560 A | 10/1995 | Stevens |
| 5,462,561 A | 10/1995 | Voda |
| 5,470,338 A | 11/1995 | Whitefield et al. |
| 5,474,572 A | 12/1995 | Hayhurst |
| 5,476,469 A | 12/1995 | Hathaway et al. |
| 5,476,470 A | 12/1995 | Fitzgibbons, Jr. |
| 5,496,332 A | 3/1996 | Sierra et al. |
| 5,499,991 A | 3/1996 | Garman et al. |
| 5,501,691 A | 3/1996 | Goldrath |
| 5,507,754 A | 4/1996 | Green et al. |
| 5,507,755 A | 4/1996 | Gresl et al. |
| 5,514,159 A | 5/1996 | Matula et al. |
| 5,520,609 A | 5/1996 | Moll et al. |
| 5,520,702 A | 5/1996 | Sauer et al. |
| 5,522,961 A | 6/1996 | Leonhardt |
| 5,527,321 A | 6/1996 | Hinchliffe |
| 5,527,322 A | 6/1996 | Klein et al. |
| 5,527,338 A | 6/1996 | Purdy |
| 5,540,658 A | 7/1996 | Evans et al. |
| 5,540,704 A | 7/1996 | Gordon et al. |
| 5,545,170 A | 8/1996 | Hart |
| 5,549,633 A | 8/1996 | Evans et al. |
| 5,558,642 A | 9/1996 | Schweich et al. |
| 5,558,644 A | 9/1996 | Boyd et al. |
| RE35,352 E | 10/1996 | Peters |
| 5,562,686 A | 10/1996 | Sauer et al. |
| 5,562,688 A | 10/1996 | Riza |
| 5,565,122 A | 10/1996 | Zinnbauer et al. |
| 5,571,090 A | 11/1996 | Sherts |
| 5,573,540 A | 11/1996 | Yoon |
| 5,584,835 A | 12/1996 | Greenfield |
| 5,584,861 A | 12/1996 | Swain et al. |
| 5,591,195 A | 1/1997 | Taheri et al. |
| 5,593,422 A | 1/1997 | Muijs Van de Moer et al. |
| 5,599,307 A | 2/1997 | Bacher et al. |
| 5,603,718 A | 2/1997 | Xu |
| 5,613,974 A | 3/1997 | Andreas et al. |
| 5,613,975 A | 3/1997 | Christy |
| 5,626,590 A | 5/1997 | Wilk |
| 5,630,833 A | 5/1997 | Katsaros et al. |
| 5,632,751 A | 5/1997 | Piraka |
| 5,632,752 A | 5/1997 | Buelna |
| 5,634,936 A | 6/1997 | Linden et al. |
| 5,637,097 A | 6/1997 | Yoon |
| 5,643,289 A | 7/1997 | Sauer et al. |
| 5,645,553 A | 7/1997 | Kolesa et al. |
| 5,662,663 A | 9/1997 | Shallman |
| 5,669,917 A | 9/1997 | Sauer et al. |
| 5,669,971 A | 9/1997 | Bok et al. |
| 5,674,198 A | 10/1997 | Leone |
| 5,681,296 A | 10/1997 | Ishida |
| 5,681,351 A | 10/1997 | Jamiolkowski et al. |
| 5,688,245 A | 11/1997 | Runge |
| 5,690,674 A | 11/1997 | Diaz |
| 5,695,468 A | 12/1997 | Lafontaine et al. |
| 5,695,504 A | 12/1997 | Gifford, III et al. |
| 5,697,905 A | 12/1997 | D'Amnbrosio |
| 5,700,273 A * | 12/1997 | Buelna .................. A61B 17/04 606/144 |
| 5,700,277 A | 12/1997 | Nash et al. |
| 5,707,379 A | 1/1998 | Fleenor et al. |
| 5,709,693 A | 1/1998 | Taylor |
| 5,716,329 A | 2/1998 | Dieter |
| 5,720,757 A | 2/1998 | Hathaway et al. |
| 5,722,983 A | 3/1998 | Van Der Weegen |
| 5,728,109 A | 3/1998 | Schulze et al. |
| 5,738,629 A | 4/1998 | Moll et al. |
| 5,743,852 A | 4/1998 | Johnson |
| 5,746,753 A | 5/1998 | Sullivan et al. |
| 5,749,883 A | 5/1998 | Halpern |
| 5,759,188 A | 6/1998 | Yoon |
| 5,766,183 A | 6/1998 | Sauer |
| 5,766,220 A | 6/1998 | Moenning |
| 5,769,870 A | 6/1998 | Salahieh et al. |
| 5,779,719 A | 7/1998 | Klein et al. |
| 5,792,152 A | 8/1998 | Klein et al. |
| 5,792,153 A | 8/1998 | Swain et al. |
| 5,795,289 A | 8/1998 | Wyttenbach |
| 5,795,325 A | 8/1998 | Valley et al. |
| 5,797,948 A | 8/1998 | Dunham |
| 5,797,960 A | 8/1998 | Stevens et al. |
| 5,810,757 A | 9/1998 | Sweezer et al. |
| 5,810,849 A | 9/1998 | Kontos |
| 5,810,850 A | 9/1998 | Hathaway et al. |
| 5,817,108 A | 10/1998 | Poncet |
| 5,817,110 A | 10/1998 | Kronner |
| 5,820,631 A | 10/1998 | Nobles |
| 5,836,955 A | 11/1998 | Buelna et al. |
| 5,843,100 A | 12/1998 | Meade |
| 5,846,251 A | 12/1998 | Hart |
| 5,846,253 A | 12/1998 | Buelna et al. |
| 5,853,399 A | 12/1998 | Sasaki |
| 5,853,422 A | 12/1998 | Huebsch et al. |
| 5,855,585 A | 1/1999 | Kontos |
| 5,860,990 A | 1/1999 | Nobles et al. |
| 5,860,991 A | 1/1999 | Klein et al. |
| 5,860,992 A | 1/1999 | Daniel et al. |
| 5,860,997 A | 1/1999 | Bonutti |
| 5,861,003 A | 1/1999 | Latson et al. |
| 5,865,729 A | 2/1999 | Holman et al. |
| 5,868,708 A | 2/1999 | Hart et al. |
| 5,868,762 A | 2/1999 | Cragg et al. |
| 5,871,537 A | 2/1999 | Holman et al. |
| 5,876,411 A | 3/1999 | Kontos |
| 5,899,921 A | 5/1999 | Caspari et al. |
| 5,902,311 A | 5/1999 | Andreas et al. |
| 5,902,321 A | 5/1999 | Caspari et al. |
| 5,906,577 A | 5/1999 | Beane et al. |
| 5,908,428 A | 6/1999 | Scirica et al. |
| 5,919,200 A | 7/1999 | Stambaugh et al. |
| 5,919,208 A | 7/1999 | Valenti |
| 5,928,192 A | 7/1999 | Maahs |
| 5,931,844 A | 8/1999 | Thompson et al. |
| 5,935,098 A | 8/1999 | Blaisdell et al. |
| 5,935,149 A | 8/1999 | Ek |
| 5,944,730 A | 8/1999 | Nobles et al. |
| 5,951,588 A | 9/1999 | Moenning |
| 5,951,590 A | 9/1999 | Goldfarb |
| 5,954,732 A | 9/1999 | Hart et al. |
| 5,967,970 A | 10/1999 | Cowan et al. |
| 5,971,983 A | 10/1999 | Lesh |
| 5,972,005 A | 10/1999 | Stalker et al. |
| 5,980,539 A | 11/1999 | Kontos |
| 5,993,466 A | 11/1999 | Yoon |
| 5,997,555 A | 12/1999 | Kontos |
| 6,001,109 A | 12/1999 | Kontos |
| 6,004,337 A | 12/1999 | Kieturakis et al. |
| 6,010,530 A | 1/2000 | Goicoechea |
| 6,015,428 A | 1/2000 | Pagedas |
| 6,024,747 A | 2/2000 | Kontos |
| 6,033,430 A | 3/2000 | Bonutti |
| 6,036,699 A | 3/2000 | Andreas et al. |
| 6,059,800 A | 5/2000 | Hart et al. |

(56) References Cited

U.S. PATENT DOCUMENTS

| | | |
|---|---|---|
| 6,066,160 A | 5/2000 | Colvin et al. |
| 6,068,648 A | 5/2000 | Cole et al. |
| 6,071,271 A | 6/2000 | Baker et al. |
| 6,077,277 A | 6/2000 | Mollenauer et al. |
| 6,086,608 A | 7/2000 | Ek et al. |
| 6,099,553 A | 8/2000 | Hart et al. |
| 6,110,185 A | 8/2000 | Barra et al. |
| 6,113,580 A | 9/2000 | Dolisi |
| 6,117,144 A | 9/2000 | Nobles et al. |
| 6,126,677 A | 10/2000 | Ganaja et al. |
| 6,136,010 A | 10/2000 | Modesitt et al. |
| 6,143,015 A | 11/2000 | Nobles |
| 6,159,234 A | 12/2000 | Bonutti et al. |
| 6,171,319 B1 | 1/2001 | Nobles et al. |
| 6,174,324 B1 | 1/2001 | Egan et al. |
| 6,187,026 B1 | 2/2001 | Devlin et al. |
| 6,190,396 B1 | 2/2001 | Whitin et al. |
| 6,200,329 B1 | 3/2001 | Fung et al. |
| 6,203,565 B1 | 3/2001 | Bonutti et al. |
| 6,210,429 B1 | 4/2001 | Vardi et al. |
| 6,217,591 B1 | 4/2001 | Egan et al. |
| 6,241,699 B1 | 6/2001 | Suresh et al. |
| 6,245,079 B1 | 6/2001 | Nobles et al. |
| 6,245,080 B1 | 6/2001 | Levinson |
| 6,248,121 B1 | 6/2001 | Nobles |
| 6,280,460 B1 | 8/2001 | Bolduc et al. |
| 6,290,674 B1 | 9/2001 | Roue et al. |
| 6,332,889 B1 | 12/2001 | Sancoff et al. |
| 6,348,059 B1 | 2/2002 | Hathaway et al. |
| 6,352,543 B1 | 3/2002 | Cole |
| 6,383,208 B1 | 5/2002 | Sancoff et al. |
| 6,409,739 B1 | 6/2002 | Nobles et al. |
| 6,432,115 B1 | 8/2002 | Mollenauer et al. |
| 6,468,293 B2 | 10/2002 | Bonutti et al. |
| 6,508,777 B1 | 1/2003 | Macoviak et al. |
| 6,527,785 B2 | 3/2003 | Sancoff et al. |
| 6,533,795 B1 | 3/2003 | Tran et al. |
| 6,537,299 B1 | 3/2003 | Hogendijk et al. |
| 6,547,725 B1 | 4/2003 | Paolitto et al. |
| 6,547,760 B1 | 4/2003 | Samson et al. |
| 6,551,331 B2 | 4/2003 | Nobles et al. |
| 6,562,052 B2 | 5/2003 | Nobles et al. |
| 6,585,689 B1 | 7/2003 | Macoviak et al. |
| 6,663,643 B2 | 12/2003 | Field et al. |
| 6,679,895 B1 | 1/2004 | Sancoff et al. |
| 6,682,540 B1 | 1/2004 | Sancoff et al. |
| 6,716,243 B1 | 4/2004 | Colvin et al. |
| 6,726,651 B1 | 4/2004 | Robinson et al. |
| 6,733,509 B2 | 5/2004 | Nobles et al. |
| 6,767,352 B2 | 7/2004 | Field et al. |
| 6,770,076 B2 | 8/2004 | Foerster |
| 6,770,084 B1 | 8/2004 | Bain et al. |
| 6,786,913 B1 | 9/2004 | Sancoff |
| 6,978,176 B2 | 1/2005 | Lattouf |
| 6,855,157 B2 | 2/2005 | Foerster et al. |
| 6,893,448 B2 | 5/2005 | O'Quinn et al. |
| 6,911,034 B2 | 6/2005 | Nobles et al. |
| 6,913,600 B2 | 7/2005 | Valley et al. |
| 6,936,057 B1 | 8/2005 | Nobles |
| 7,004,952 B2 | 2/2006 | Nobles et al. |
| 7,083,630 B2 | 8/2006 | DeVries et al. |
| 7,083,638 B2 | 8/2006 | Foerster |
| 7,090,686 B2 | 8/2006 | Nobles et al. |
| 7,090,690 B2 | 8/2006 | Foerster et al. |
| 7,118,583 B2 | 10/2006 | O'Quinn et al. |
| 7,160,309 B2 | 1/2007 | Voss |
| 7,172,595 B1 | 2/2007 | Goble |
| 7,220,266 B2 | 5/2007 | Gambale |
| 7,232,446 B1 | 6/2007 | Farris |
| 7,235,086 B2 | 6/2007 | Sauer et al. |
| 7,326,221 B2 | 2/2008 | Sakamoto et al. |
| 7,329,272 B2 | 2/2008 | Burkhart et al. |
| 7,338,502 B2 | 3/2008 | Rosenblatt |
| 7,381,210 B2 | 6/2008 | Zarbatany et al. |
| 7,399,304 B2 | 7/2008 | Gambale et al. |
| 7,435,251 B2 | 10/2008 | Green |
| 7,449,024 B2 | 11/2008 | Stafford |
| 7,491,217 B1 | 2/2009 | Hendren |
| 7,601,161 B1 | 10/2009 | Nobles et al. |
| 7,628,797 B2 | 12/2009 | Tieu et al. |
| 7,635,386 B1 | 12/2009 | Gammie |
| 7,637,926 B2 | 12/2009 | Foerster et al. |
| 7,722,629 B2 | 5/2010 | Chambers |
| 7,803,167 B2 | 9/2010 | Nobles et al. |
| 7,842,051 B2 | 11/2010 | Dana et al. |
| 7,846,181 B2 | 12/2010 | Schwartz et al. |
| 7,879,072 B2 | 2/2011 | Bonutti et al. |
| 7,905,892 B2 | 3/2011 | Nobles et al. |
| 7,918,867 B2 | 4/2011 | Dana et al. |
| 7,931,641 B2 | 4/2011 | Chang et al. |
| 7,993,368 B2 | 8/2011 | Gambale et al. |
| 8,075,573 B2 | 12/2011 | Gambale et al. |
| 8,083,754 B2 | 12/2011 | Pantages et al. |
| 8,105,355 B2 | 1/2012 | Page et al. |
| 8,197,497 B2 | 6/2012 | Nobles et al. |
| 8,202,281 B2 | 6/2012 | Voss |
| 8,246,636 B2 | 8/2012 | Nobles et al. |
| 8,258,005 B2 | 8/2012 | Findley, III et al. |
| 8,282,659 B2 | 10/2012 | Oren et al. |
| 8,287,556 B2 | 10/2012 | Gilkey et al. |
| 8,298,291 B2 | 10/2012 | Ewers et al. |
| 8,303,622 B2 | 11/2012 | Alkhatib |
| 8,348,962 B2 | 1/2013 | Nobles et al. |
| 8,372,089 B2 | 2/2013 | Nobles et al. |
| 8,398,676 B2 | 3/2013 | Roorda et al. |
| 8,430,893 B2 | 4/2013 | Ma |
| 8,469,975 B2 | 6/2013 | Nobles et al. |
| 8,496,676 B2 | 7/2013 | Nobles et al. |
| 8,500,776 B2 | 8/2013 | Ebner |
| 8,540,736 B2 | 9/2013 | Gaynor et al. |
| 8,568,427 B2 | 10/2013 | Nobles et al. |
| 8,623,036 B2 | 1/2014 | Harrison et al. |
| 8,728,105 B2 | 5/2014 | Aguirre |
| 8,758,370 B2 | 6/2014 | Shikhman et al. |
| 8,771,296 B2 | 7/2014 | Nobles et al. |
| 9,131,938 B2 | 9/2015 | Nobles et al. |
| 9,326,764 B2 | 5/2016 | Nobles et al. |
| 9,332,976 B2 | 5/2016 | Yribarren |
| 9,364,238 B2 | 6/2016 | Bakos et al. |
| 9,398,907 B2 | 7/2016 | Nobles et al. |
| 9,402,605 B2 | 8/2016 | Viola |
| 9,649,106 B2 | 5/2017 | Nobles et al. |
| 9,706,988 B2 | 7/2017 | Nobles et al. |
| 10,178,993 B2 | 1/2019 | Nobles et al. |
| 10,182,802 B2 | 1/2019 | Nobles et al. |
| 10,194,902 B2 | 2/2019 | Nobles et al. |
| 10,285,687 B2 | 5/2019 | Nobles et al. |
| 10,420,545 B2 | 9/2019 | Nobles et al. |
| 10,512,458 B2 | 12/2019 | Nobles |
| 10,610,216 B2 | 4/2020 | Nobles et al. |
| 10,624,629 B2 | 4/2020 | Nobles et al. |
| 2001/0031973 A1 | 10/2001 | Nobles et al. |
| 2002/0013601 A1 | 1/2002 | Nobles et al. |
| 2002/0045908 A1 | 4/2002 | Nobles et al. |
| 2002/0049453 A1 | 4/2002 | Nobles et al. |
| 2002/0111653 A1 | 5/2002 | Foerster |
| 2002/0087178 A1 | 7/2002 | Nobles et al. |
| 2002/0096183 A1 | 7/2002 | Stevens et al. |
| 2002/0128598 A1 | 9/2002 | Nobles |
| 2002/0169475 A1 | 11/2002 | Gainor et al. |
| 2002/0183787 A1 | 12/2002 | Wahr et al. |
| 2003/0078601 A1 | 4/2003 | Skikhman et al. |
| 2003/0114863 A1 | 6/2003 | Field et al. |
| 2003/0144673 A1 | 7/2003 | Onuki et al. |
| 2003/0204205 A1 | 10/2003 | Sauer et al. |
| 2003/0208209 A1 | 11/2003 | Gambale et al. |
| 2003/0220667 A1 | 11/2003 | van der Burg et al. |
| 2004/0015177 A1 | 1/2004 | Chu |
| 2004/0044365 A1 | 3/2004 | Bachman |
| 2004/0059351 A1 | 3/2004 | Eigler et al. |
| 2004/0153116 A1 | 8/2004 | Nobles |
| 2004/0236356 A1 | 11/2004 | Rioux et al. |
| 2004/0260298 A1 | 12/2004 | Kaiseer et al. |
| 2005/0070923 A1 | 3/2005 | McIntosh |

(56) References Cited

U.S. PATENT DOCUMENTS

| | | |
|---|---|---|
| 2005/0149066 A1 | 7/2005 | Stafford |
| 2005/0187575 A1 | 8/2005 | Hallbeck et al. |
| 2005/0203564 A1 | 9/2005 | Nobles |
| 2005/0228407 A1 | 10/2005 | Nobles et al. |
| 2005/0261708 A1 | 11/2005 | Pasricha et al. |
| 2005/0261710 A1 | 11/2005 | Sakamoto et al. |
| 2005/0277986 A1 | 12/2005 | Foerster et al. |
| 2006/0052813 A1 | 3/2006 | Nobles |
| 2006/0064113 A1 | 3/2006 | Nakao |
| 2006/0064115 A1 | 3/2006 | Allen et al. |
| 2006/0069397 A1 | 3/2006 | Nobles et al. |
| 2006/0074484 A1 | 4/2006 | Huber |
| 2006/0095052 A1 | 5/2006 | Chambers |
| 2006/0195120 A1 | 8/2006 | Nobles et al. |
| 2006/0265010 A1 | 11/2006 | Paraschac et al. |
| 2006/0282088 A1 | 12/2006 | Ryan |
| 2006/0282094 A1 | 12/2006 | Stokes et al. |
| 2006/0282102 A1 | 12/2006 | Nobles et al. |
| 2006/0287657 A1 | 12/2006 | Bachman |
| 2007/0005079 A1 | 1/2007 | Zarbatany et al. |
| 2007/0010829 A1 | 1/2007 | Nobles et al. |
| 2007/0043385 A1 | 2/2007 | Nobles et al. |
| 2007/0060930 A1 | 3/2007 | Hamilton et al. |
| 2007/0106310 A1 | 5/2007 | Goldin et al. |
| 2007/0118151 A1 | 5/2007 | Davidson |
| 2007/0142846 A1 | 6/2007 | Catanese, III et al. |
| 2007/0213757 A1 | 9/2007 | Boraiah |
| 2007/0219630 A1 | 9/2007 | Chu |
| 2007/0276413 A1 | 11/2007 | Nobles |
| 2007/0276414 A1 | 11/2007 | Nobles |
| 2008/0033459 A1 | 2/2008 | Shafi et al. |
| 2008/0077162 A1 | 3/2008 | Domingo |
| 2008/0114384 A1 | 5/2008 | Chang et al. |
| 2008/0188873 A1 | 8/2008 | Speziali |
| 2008/0228201 A1 | 9/2008 | Zarbatany |
| 2008/0269786 A1 | 10/2008 | Nobles et al. |
| 2008/0269788 A1 | 10/2008 | Phillips |
| 2009/0036906 A1 | 2/2009 | Stafford |
| 2009/0048615 A1 | 2/2009 | McIntosh |
| 2009/0099410 A1 | 4/2009 | De Marchena |
| 2009/0105729 A1 | 4/2009 | Zentgraf |
| 2009/0105751 A1 | 4/2009 | Zentgraf |
| 2009/0118726 A1 | 5/2009 | Auth et al. |
| 2009/0125042 A1 | 5/2009 | Mouw |
| 2009/0287183 A1 | 11/2009 | Bishop et al. |
| 2009/0299409 A1 | 12/2009 | Coe et al. |
| 2009/0312772 A1 | 12/2009 | Chu |
| 2009/0312783 A1 | 12/2009 | Whayne et al. |
| 2009/0312789 A1 | 12/2009 | Kassab et al. |
| 2010/0016870 A1 | 1/2010 | Campbell |
| 2010/0030242 A1 | 2/2010 | Nobles et al. |
| 2010/0042147 A1 | 2/2010 | Janovsky et al. |
| 2010/0063586 A1 | 3/2010 | Hasenkam et al. |
| 2010/0087838 A1 | 4/2010 | Nobles et al. |
| 2010/0094314 A1 | 4/2010 | Hernlund et al. |
| 2010/0100167 A1 | 4/2010 | Bortlein et al. |
| 2010/0179585 A1 | 7/2010 | Carpenter et al. |
| 2010/0210899 A1 | 8/2010 | Schankereli |
| 2011/0190793 A1 | 8/2011 | Nobles et al. |
| 2011/0251627 A1 | 10/2011 | Hamilton et al. |
| 2012/0016384 A1 | 1/2012 | Wilke et al. |
| 2012/0035628 A1 | 2/2012 | Aguirre et al. |
| 2012/0143222 A1 | 6/2012 | Dravis et al. |
| 2012/0165838 A1 | 6/2012 | Kobylewski et al. |
| 2012/0296373 A1 | 11/2012 | Roorda et al. |
| 2013/0103056 A1 | 4/2013 | Chu |
| 2013/0261645 A1 | 10/2013 | Nobles et al. |
| 2013/0324800 A1 | 12/2013 | Cahill |
| 2014/0148825 A1* | 5/2014 | Nobles ............... A61B 17/0469 606/145 |
| 2014/0163585 A1 | 6/2014 | Nobles et al. |
| 2014/0303654 A1 | 10/2014 | Nobles et al. |
| 2014/0309670 A1 | 10/2014 | Bakos et al. |
| 2014/0379006 A1 | 12/2014 | Sutherland et al. |
| 2015/0126815 A1 | 5/2015 | Nobles |
| 2015/0359531 A1 | 12/2015 | Sauer |
| 2016/0007998 A1 | 1/2016 | Nobles et al. |
| 2016/0302787 A1 | 10/2016 | Nobles |
| 2017/0035425 A1 | 2/2017 | Fegelman et al. |
| 2017/0049451 A1 | 2/2017 | Hausen |
| 2017/0296168 A1 | 4/2017 | Nobles et al. |
| 2017/0128059 A1 | 5/2017 | Coe et al. |
| 2017/0245853 A1 | 8/2017 | Nobles |
| 2017/0303915 A1 | 10/2017 | Nobles |
| 2019/0029672 A1 | 1/2019 | Nobles et al. |
| 2019/0150903 A1 | 5/2019 | Nobles |
| 2019/0239880 A1 | 8/2019 | Nobles |

FOREIGN PATENT DOCUMENTS

| | | |
|---|---|---|
| CN | 101257852 | 8/2011 |
| CN | 102892359 A | 1/2013 |
| DE | 29 01 701 | 7/1980 |
| EP | 0 241 038 | 10/1987 |
| EP | 0 544 485 | 6/1993 |
| EP | 0839 550 | 5/1998 |
| EP | 0 894 475 | 2/1999 |
| EP | 1 196 093 | 4/2002 |
| EP | 1 303 218 | 4/2003 |
| EP | 0 941 698 | 5/2005 |
| EP | 0 983 027 | 12/2005 |
| EP | 1 852 071 | 11/2007 |
| EP | 1 987 779 | 11/2008 |
| EP | 2 572 649 | 3/2013 |
| FR | 2 701 401 | 8/1994 |
| JP | A 9507398 | 7/1997 |
| JP | 09-266910 A | 10/1997 |
| JP | H10-43192 | 2/1998 |
| JP | 2001-524864 | 12/2001 |
| JP | 2003-225241 A | 8/2003 |
| JP | 2007-503870 | 3/2007 |
| JP | 2008-514305 | 5/2008 |
| JP | 2008-541857 | 11/2008 |
| JP | 2008-546454 | 12/2008 |
| JP | 2009-261960 | 11/2009 |
| JP | 2010-522625 | 7/2010 |
| JP | 2011-067251 | 4/2011 |
| JP | 5848125 | 12/2015 |
| RU | 2010 125954 | 1/2012 |
| SU | 1560129 A1 | 4/1990 |
| WO | WO 92/05828 | 4/1992 |
| WO | WO 93/01750 | 2/1993 |
| WO | WO 93/07800 | 4/1993 |
| WO | WO 95/12429 | 5/1995 |
| WO | WO 95/17127 | 6/1995 |
| WO | WO 95/25468 | 9/1995 |
| WO | WO 95/25470 | 9/1995 |
| WO | WO 96/03083 | 2/1996 |
| WO | WO 96/29012 | 9/1996 |
| WO | WO 96/40347 | 12/1996 |
| WO | WO 97/03613 | 2/1997 |
| WO | WO 97/47261 | 2/1997 |
| WO | WO 97/07745 | 3/1997 |
| WO | WO 97/12540 | 4/1997 |
| WO | WO 97/20505 | 6/1997 |
| WO | WO 97/24975 | 7/1997 |
| WO | WO 97/27807 | 8/1997 |
| WO | WO 97/40738 | 11/1997 |
| WO | WO 98/12970 | 4/1998 |
| WO | WO 98/52476 | 11/1998 |
| WO | WO 99/40851 | 8/1999 |
| WO | WO 99/42160 | 8/1999 |
| WO | WO 99/45848 | 9/1999 |
| WO | WO 00/002489 | 1/2000 |
| WO | WO 01/001868 | 1/2001 |
| WO | WO 01/95809 | 12/2001 |
| WO | WO 02/024078 | 3/2002 |
| WO | WO 04/012789 | 2/2004 |
| WO | WO 06/127636 | 11/2006 |
| WO | WO 07/001936 | 1/2007 |
| WO | WO 09/081396 | 7/2009 |
| WO | WO 11/094619 | 8/2011 |
| WO | WO 11/156782 | 12/2011 |
| WO | WO 12/012336 | 1/2012 |

(56) References Cited

FOREIGN PATENT DOCUMENTS

| WO | WO 13/027209 | 2/2013 |
|---|---|---|
| WO | WO 13/142487 | 9/2013 |
| WO | WO 15/002815 | 1/2015 |
| WO | WO 15/085145 | 6/2015 |
| WO | WO 17/180092 | 10/2017 |
| WO | WO 19/035095 | 2/2019 |
| WO | WO 19/051379 | 3/2019 |
| WO | WO 19/055433 | 3/2019 |

OTHER PUBLICATIONS

Cardio Medical Solutions, Inc. brochure titled: "Baladi Inverter for Clamp less Surgery"—Undated.

Clinical Evaluation of Arteriovenous Fistulas as an Adjunct to Lower Extremity Arterial Reconstructions, by Herbert Dardick, M.D., in Current Critical Problems in Vascular Surgery, copyright 1989 by Quality Medical Publishing Inc., at p. 383.

Current Therapy in Vascular Surgery, 2nd edition, by Calvin B. Ernst, M.D. and James C. Stanley, M.D., copyright 1991 by B.C. Decker, Inc., at pp. A and 140.

Eskuri, A., The Design of a Minimally Invasive Vascular Suturing Device, Thesis submitted to Rose-Hulman Institute of Technology, Nov. 1999.

Manual of Vascular Surgery, vol. 2, Edwin J. Wylie, Ronald J. Stoney, William K. Ehrenfeld and David J. Effeney (Richard H. Egdahl ed.), copyright 1986 by Springer-Verlag New York Inc., at p. 41.

Nursing the Open-Heart Surgery Patient, by Mary Jo Aspinall, R.N., M.N., copyright 1973 by McGraw Hill, Inc., at pp. 216 and 231.

Operative Arterial Surgery, by P.R. Bell, M.D., and W Barrie, M.D., copyright 1981 by Bell, Barrie, and Leicester Royal Infirmary, printed byJohn Wright &Sons, pp. 16, 17, 104, 105, 112, and 113.

Sinus Venous Type of Atrial Septal Defect with Partial Anomalous Pulmonary Venous Return, by Francis Robicsek, MD., et ai, in Journal of Thoracic and Cardiovascular Surgery, Oct. 1979, vol. 78, No. 4, at pp. 559-562.

Techniques in Vascular Surgery, by Denton A. Cooley, MD. and Don C. Wukasch, MD., copyright 1979 by WB. Saunders Co., at pp. 38,57,86,134,156, and 184.

The problem: Closing wounds in deep areas during laparoscopic operations The solution: REMA Medizintechnik GmbH (no date).

Vascular Access, Principles and Practice, 3rd edition, by Samuel Eric Wilson, MD., copyright 1996, 1988,1980 by Mosby-Year Book, Inc., pp. 89 and 159.

Vascular and Endovascular Surgery, by Jonathan D. Beard and Peter Gainers, copyright 1998 by W. B. Saunders Co., Ltd, p. 414.

Vascular Surgery, 3rd edition, vol. 1, by Robert B. Rutherford, MD., copyright 1989, 1984, 1976 by W. B.SaundersCo., at pp. 347, 348, 354, 594, 607, 622, 675, 677, 680, 698, 700, 721, 727, 735, and 829.

Vascular Surgery, 4th edition by Robert B. Rutherford, MD., copyright 1995,1989,1976, by W.B. Saunders Co., vol. 1, at pp. 400-404, 661, and A.

Vascular Surgery, 4th edition, by Robert B. Rutherford, M.D., copyright 1995, 1989, 1984, 1976 by W. B. Saunders Co., vol. 2, at pp. 1318, 1363, 1426, 1564, and 1580.

Vascular Surgery, by Robert B. Rutherford, M.D. copyright1977 by WB. Saunders Co., at pp. 334 and 817.

International Search Report and Written Opinion re PCT Application No. PCT/US2014/044429, dated Nov. 4, 2014.

International Preliminary Report on Patentability re PCT Application No. PCT/US2014/044429, dated Jan. 5, 2016.

European Supplemental Search Report for European Application No. 14819989.6, dated Apr. 11, 2017.

European Exam Report re EP Application No. 18199178.7, dated Mar. 21, 2019.

Search Report in corresponding Eurasian Patent Application No. 201990049, dated May 14, 2019, in 1 page.

* cited by examiner

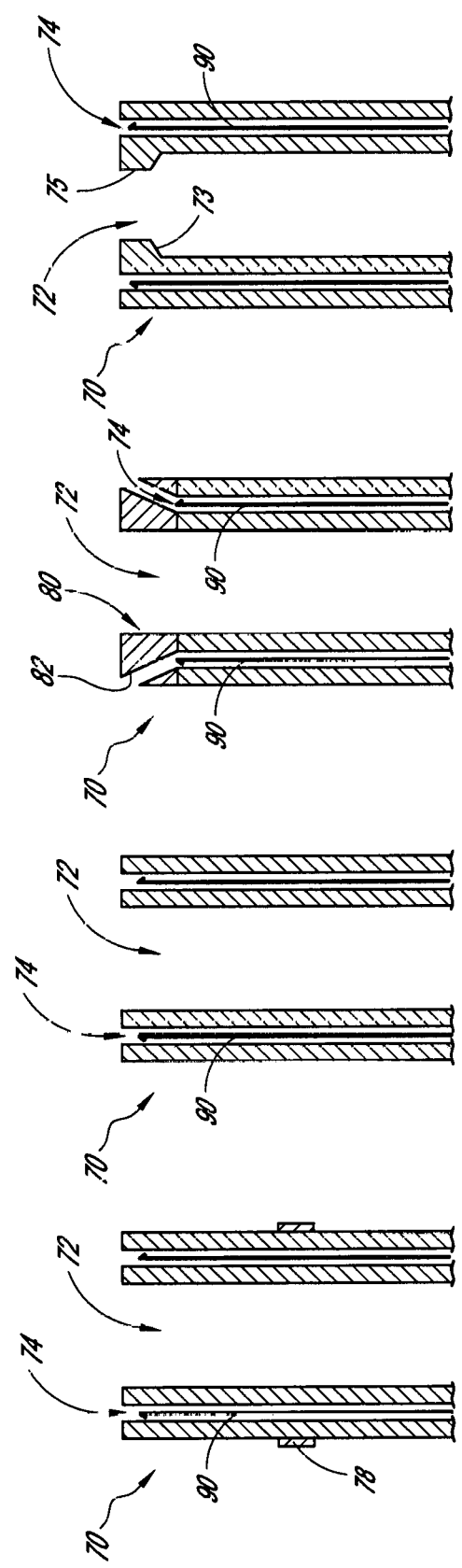

SUTURING DEVICES AND METHODS FOR SUTURING AN ANATOMIC STRUCTURE

TECHNICAL FIELD

Embodiments of the present invention relate to suturing devices and methods. Some embodiments relate to suturing devices and methods for suturing a patient's vasculature

BACKGROUND

Health practitioners frequently use sutures to close various openings such as natural anatomical openings, cuts, punctures, and incisions in various places in the human body. Generally, sutures are convenient to use and function properly to hold openings in biological tissue closed thereby aiding in blood clotting, healing, and prevention of scarring.

There are some circumstances under which it is not feasible to use conventional sutures and suturing methods to close an opening. Additionally, there are some circumstances under which the use of conventional sutures and suturing methods require invasive procedures that subject a patient to risk of infection, delays in recovery, increases in pain, and other complications.

SUMMARY OF THE DISCLOSURE

Embodiments of suturing devices and methods used to apply sutures and/or to suture closed openings at, within, or into a biological structure while maintaining or substantially maintaining haemostasis are described herein. The suturing devices and methods can be used to place sutures prior to a surgical procedure and to prepare access for the procedure while maintaining or substantially maintaining haemostasis. The placed sutures can then be used to tighten an opening while any devices or tools are withdrawn, closing the opening while the final device or tool leaves the opening such that the opening is never without a device or tool inside it during the course of the procedure.

In the embodiments described herein, the disclosed devices are used to place sutures to close an opening into a patient's vasculature, such as the aorta, although they are not limited to applications within the vasculature. The aorta can be accessed through a sternotomy or limited thoracotomy, or alternatively the device can pass through a trocar or other element into the thoracic cavity and then be led toward an opening in the aorta, typically by following a guide wire.

In some embodiments, a suturing device can include an elongate body having a proximal end and a distal end, and a plurality of arms near the distal end. Each arm can be configured to move between a first position in which the arm is retracted within the elongate body and a second position in which the arm has a free end extending away from the elongate body. Each arm can also include at least one suture mount at the free end. A sheath can be adapted to surround at least a portion of the elongate body. The device can also include a needle carriage that has a plurality of outer lumens and a central lumen adapted to surround at least a portion of the sheath. The device can include a plurality of needles, and each needle can be configured to move between a retracted position in which the needle is within a corresponding outer lumen to a deployed position in which a distal point of the needle extends out of the corresponding outer lumen and into a corresponding suture mount. The device can include a plurality of suture portions, and each suture portion can have a suture end releasably retained within a suture mount of a corresponding arm of the plurality of arms.

In various embodiments a suturing system can comprise a suturing device having an elongate body with a proximal end and a distal end. The device can include a first plurality of arms near the distal end and each arm can be configured to move between a first position wherein the arm is retracted within the elongate body and a second position wherein the arm has a free end extending away from the elongate body. Each arm can have at least one suture mount at the free end. The device can also have a second plurality of arms proximal to the first plurality of arms. Each arm of the second plurality of arms can be configured to move between a first position wherein the arm is retracted within the elongate body, and a second position wherein the arm has a free end extending away from the elongate body. A sheath can be adapted to surround at least a portion of the elongate body. The device can include a plurality of needles, and each needle can be configured to move between a retracted position in which a distal point of the needle is proximal to the second plurality of arms and a deployed position in which the distal point of the needle extends through an arm of the second plurality of arms and a corresponding suture mount. The device can also have a plurality of suture portions, each suture portion having a suture end that is releasably retained within a suture mount of a corresponding arm of the first plurality of arms.

Methods of use are also described. In some embodiments, a suturing system can be delivered through an opening in the wall of a blood vessel and into the blood vessel. The suturing system can include a suturing device with an elongate body having a proximal end and a distal end, a plurality of arms near the distal end, a sheath at least partially surrounding the elongate body, and a plurality of needles positioned at least partially within a needle carriage that surrounds at least a portion of the elongate body. The needle carriage can be further configured to surround at least a portion of the sheath.

The plurality of arms can be extended from the elongate body of the suturing device, each of the arms carrying a suture portion having a suture end releasably retained in a respective arm. The plurality of arms can be positioned against an inside surface of the wall of the blood vessel, and the needle carriage can be advanced into a position aligned with the plurality of arms. The plurality of needles can be advanced from the needle carriage through the wall of the blood vessel, each needle aligned with a respective suture mount located in a respective arm and engaging a respective suture portion positioned in the respective suture mount. The needles can be retracted through the wall of the blood vessel to draw the respective suture ends through the wall of the blood vessel. The needle carriage can be retracted to withdraw the suture ends engaged by the needles to a location outside of the patient. The sheath can be advanced at least partially through the wall of the blood vessel, the plurality of arms can be retracted into the elongate body of the suturing device, and the elongate body can be withdrawn from the blood vessel while leaving the sheath at least partially within the wall of the blood vessel.

In some embodiments, a suturing system can be delivered through an opening in a biological structure. The suturing system can comprise an elongate body having a proximal end and a distal end, a plurality of arms near the distal end, and a sheath at least partially surrounding the elongate body. The plurality of arms can be extended from the elongate body of the suturing device, each of the arms carrying a suture portion having a suture end releasably retained in a respective arm. The arms can be positioned against or near an interior surface of the biological structure and a plurality of needles can be advanced from a position outside of the biological structure and outside of the sheath through tissue of the biological structure to engage the suture ends releasably retained in the respective arms. The plurality of needles can be retracted through the tissue of the biological structure to draw the respective suture ends through the tissue of the biological structure. The needle carriage can be retracted to withdraw the suture ends engaged by the needles to a location outside of the patient. The sheath can be advanced at least partially through the opening in the biological structure. The plurality of arms can be retracted into the elongate body of the suturing device and the elongate body can be withdrawn from the biological structure while leaving the sheath at least partially within the opening of the biological structure.

BRIEF DESCRIPTION OF THE DRAWINGS

The above-mentioned and other features disclosed herein are described below with reference to the drawings of specific embodiments. The illustrated embodiments are intended for illustration, but not limitation. The drawings contain the following figures:

FIGS. 4A through 4D illustrate cross-sectional views of the needle carriages of FIGS. 3A through 3D, respectively.

DETAILED DESCRIPTION OF SPECIFIC EMBODIMENTS

Embodiments of suturing devices and methods used to apply sutures and/or suture closed openings at, within, or into a biological structure while maintaining or substantially maintaining haemostasis are described herein. The suturing devices and methods can be used to place sutures prior to performing a surgical procedure and to prepare access for the procedure while maintaining or substantially maintaining haemostasis. The placed sutures can then be used to tighten an opening while any devices or tools are withdrawn, closing the opening while the final device or tool leaves the opening such that the opening is never without a device or tool inside it during the course of the procedure. Embodiments described herein can be used to provide access to and/or suture an access opening to a biological structure where space outside of the biological structure is limited, such as the aorta.

In the embodiments described herein, the disclosed devices are used to place sutures to close an opening into an aorta, although they are not limited to applications within the aorta or the vasculature generally. The aorta can be accessed through a sternotomy or limited thoracotomy, or alternatively the device can pass through a trocar or other element into the thoracic cavity and then be led toward a puncture in the aorta, typically by following a guide wire.

In some embodiments, the suturing devices can be used to close or reduce a variety of other tissue openings, lumens, hollow organs, or natural or surgically created passageways in the body. In some embodiments, the suturing devices can be used to suture prosthetics, synthetic materials, or implantable devices in the body. For example, the devices can be used to suture a pledget within the body.

Further details of suturing devices and methods that may be used to suture openings in a biological structure can be found in U.S. Patent Publication No. 2011/0190793 A1, published Aug. 4, 2011, which is hereby incorporated by reference in its entirety and a copy of which is enclosed and is included as part of this specification. Features and procedures described in the aforementioned publication can be incorporated into the embodiments described herein.

Figure 1:
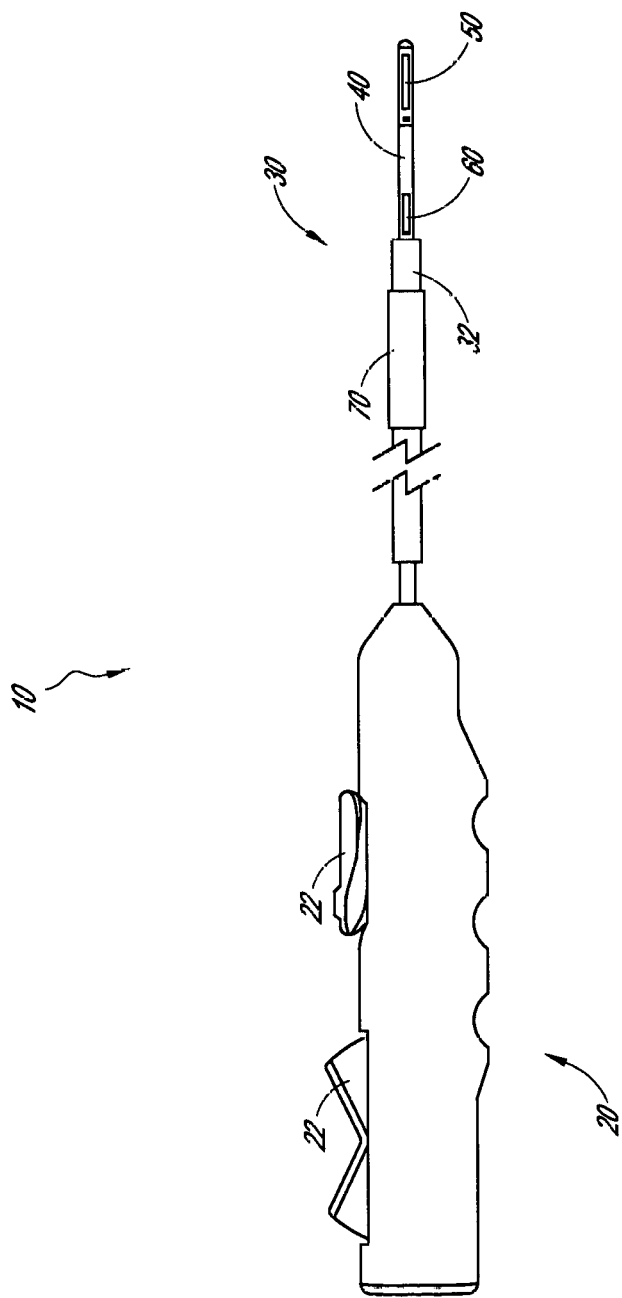
FIG. 1 is a schematic drawings of one embodiment of a suturing system for suturing an anatomic structure.

FIG. 1 illustrates one embodiment of a suturing device 10 that can be used to insert sutures through the wall of a biological structure in anticipation of performing a surgical procedure in or through the biological structure while maintaining hemostasis. In some embodiments the device can be used to insert sutures through the wall of a blood vessel, such as the aorta. The device may comprise one or more elongate bodies and has a proximal and a distal end. At the proximal end, the suturing device can include a handle 20 with various actuation elements 22, such as buttons or levers, that can be used to control various components of the device. Further details regarding handles and associated components, including actuator rods, are provided in U.S. Patent Application Publication No. 2008/0269786, published on Oct. 30, 2008, which is hereby incorporated by reference herein in its entirety.

At the distal end of the suturing device 10, the suturing device can include a distal assembly 30. The distal assembly can include an elongate body 40 that has a distal end and a proximal end. The distal assembly can also include one or more distal suture arms 50 and one or more proximal extensions or arms 60 that are positioned proximal to the distal suture arms. When the device is assembled, it can also include a sheath 32 that surrounds at least a portion of the elongate body, and an outer sleeve or needle carriage 70 that also surrounds at least a portion of the elongate body. As described further below, in some embodiments the needle carriage can include one or more suture catch mechanisms or needles.

In some embodiments, the sheath and/or the needle carriage can move axially relative to the elongate body. In some embodiments, the needle carriage 70 can surround at least a portion of the sheath 32 when the device is assembled. Preferably, the needle carriage can rotate relative to the sheath and/or the elongate body, but in some embodiments the needle carriage can have a fixed orientation relative to the sheath and/or the elongate body. In some embodiments, as described further below, a suturing device can have elements such as mechanical stops and/or detents that provide an indexing or alignment function, allowing an operator of the device to determine when the needle carriage has been moved and/or rotated into a desired position.

Figure 2A:
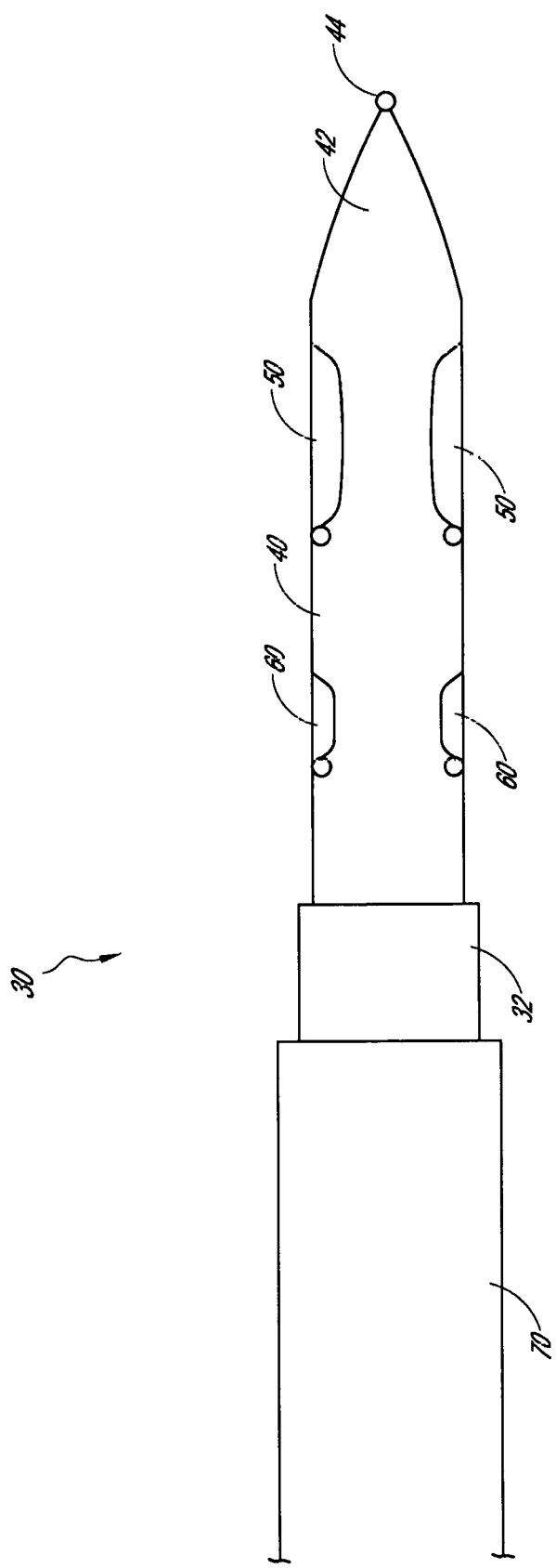
FIG. 2A is a schematic drawing of a distal assembly of a suturing system having a first and second set of arms in a retracted position.
Figure 2B:
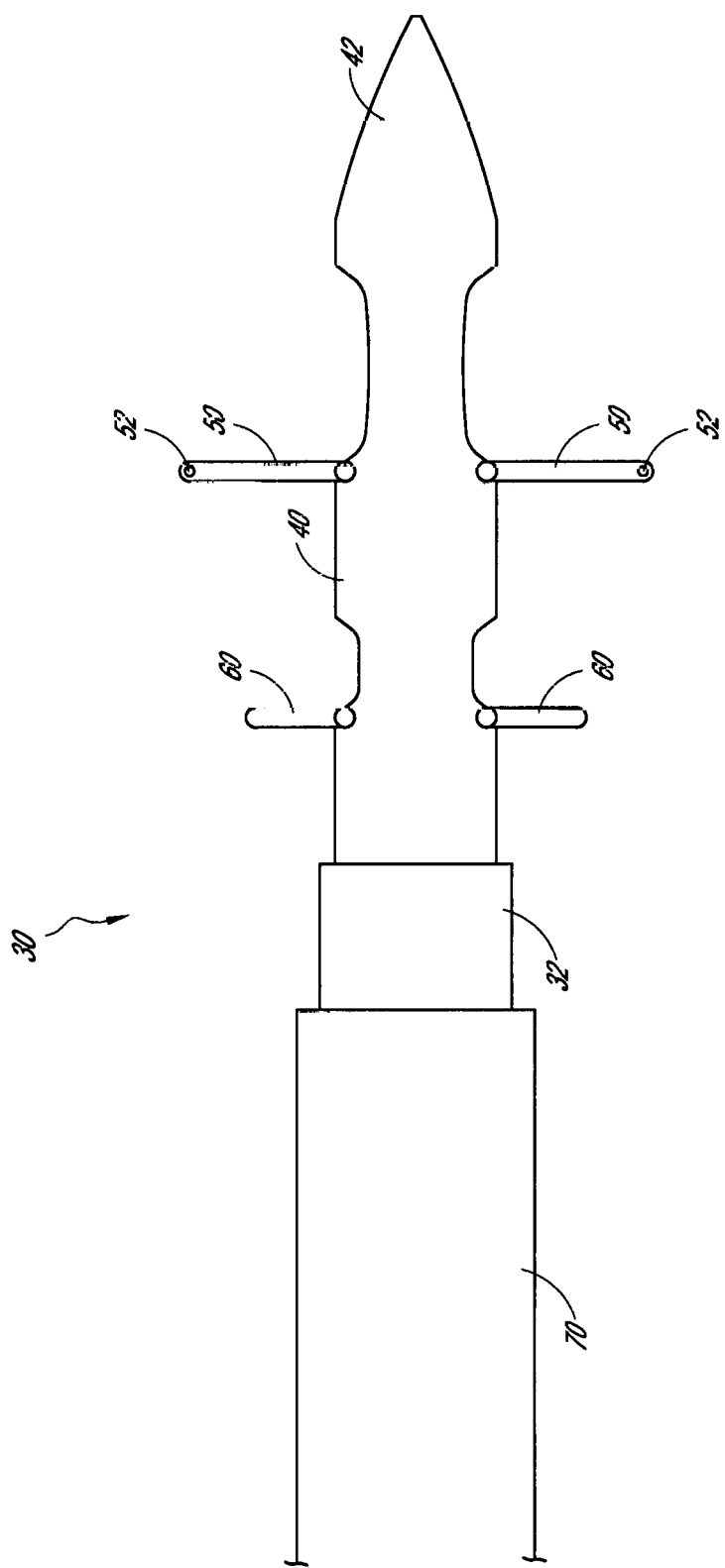
FIG. 2B is a schematic drawing of the distal assembly of FIG. 2 with the first and second arms in an extended position.

FIGS. 2A and 2B illustrate a perspective view of the distal assembly 30. As illustrated, in some embodiments a distal assembly can include a plurality of distal arms 50 and a plurality of proximal extensions 60 that can also be arms. FIG. 2A illustrates the distal and proximal arms in a retracted position, in which the arms are at least partially within the elongate body 40. In FIG. 2B, the distal and proximal arms are illustrated in an extended position, in which the arms extend outward from the elongate body. In some embodiments, as illustrated, the arms can extend from the elongate body at approximately a 90 degree angle, but in other embodiments the arms can extend at an angle less than 90 degrees. In some embodiments, the proximal arms in an extended position may extend from the elongate body at approximately a 90 degree angle, while the distal arms in an extended position may extend from the elongate body at an angle less than 90 degrees. In some embodiments, the distal arms may extend from the elongate body in the extended position at approximately 90 degrees, while the proximal arms extend from the elongate body in the extended position at an angle less than 90 degrees In various embodiments the distal assembly 30 can have a varying number of arms 50, 60. In some embodiments the distal assembly has four distal arms 50 spaced approximately 90 degrees apart from each other and four proximal arms 60 spaced approximately 90 degrees from each other. In some embodiments the distal assembly can comprise fewer than four distal arms 50, such as two distal arms, or more than four distal arms. In some embodiments, for each distal arm there can be a second distal arm positioned 180 degrees about the elongate body from the first distal arm.

In some embodiments the distal assembly can comprise fewer than four proximal extensions or arms 60, such as two proximal arms, or more than four proximal arms. In some embodiments, for each proximal arm there can be a second proximal arm positioned 180 degrees about the elongate body from the first proximal arm. In some embodiments, the distal assembly has the same number of proximal arms as distal arms, though in some embodiments they differ in number. In some embodiments, each proximal arm can be aligned with a corresponding distal arm along a line parallel to a longitudinal axis of the elongate body 40.

In some embodiments, the proximal extensions or arms 60 can be one or more extensions that extend circumferentially around a portion of the elongate body 40. In some embodiments, proximal extensions can each extend around a quarter, a third, or a half of the circumference of the elongate body. In some embodiments, proximal extensions 60 can be a single extension. The single extension can wrap around the circumference of the elongate body. As described above, proximal extensions can have a retracted position in which the extensions are within the elongate body and an extended position in which they extend out of the elongate body. Also as described above, the extensions can extend from the elongate body at varying angles when in the extended position, including at 90 degrees.

As further illustrated in FIGS. 2A and 2B, in some embodiments the elongate body 40 can include a tapered distal tip 42. The tapered tip can help when inserting the elongate body into or through biological tissue. The elongate body can also have a central lumen 44 that can be used to receive a guidewire, as discussed further below.

As illustrated in FIG. 2B, the distal arms 50 may be distal suture arms 50 that include one or more suture mounts or clasps 52 at a distal end of the suture arms. The suture clasps 52 can be adapted to releasably retain a suture portion, as described further below. In some embodiments, a suture portion can run from inside the elongate body along the length of an arm 50 to a suture clasp. As illustrated, when the distal suture arms 50 and the proximal extensions or arms 60 rotate from the retracted to the extended position, or from the extended to the retracted position, a free end of the arms will move towards a distal end of the elongate body. In some embodiments, the suture arms 50 and/or the extensions or arms 60 can be configured to rotate from the retracted to the extended position, or from the extended to the retracted position, such that as the arms rotate from the extended to the retracted position their free ends will move towards a proximal end of the suturing device. In some embodiments, the arms can slide or move in other ways from the retracted to the extended position or from the extended to the retracted position.

In some embodiments, the distal suture arms 50 can simultaneously move from a retracted to an extended position or from an extended to a retracted position. In some embodiments, the arms 50 can move independently. Similarly, in some embodiments the proximal extensions or arms 60 can move independently or simultaneously.

In some embodiments, the proximal extensions or arms 60 can be shorter than the distal suture arms 50. In some embodiments, when the proximal extensions or arms 60 are in an extended position, their distal ends can be closer to the elongate body than the distal ends of the distal suture arms 50 are when the distal suture arms are in an extended position. This can help minimize the space that the device requires outside of a biological structure.

FIGS. 3A through 3D illustrate various embodiments of the needle carriage 70. It is understood that various features, components, or other elements discussed with respect to any of these embodiments is not limited to the particular embodiment in which it appears, but can be included in combination with features, components, or elements illustrated or discussed with respect to any other described embodiment. Generally, the outer sleeve or needle carriage 70 includes a central lumen 72 and one or more outer lumens 74. One or more of the outer lumens can be used to house a suture catch mechanism or needle 90, as illustrated and described in more detail below. In some embodiments, the needle carriage 70 can have four outer lumens spaced symmetrically about a central axis of the needle carriage. In some embodiments, the needle carriage can have more than four or fewer than four outer lumens. In some embodiments, the needle carriage can have as many outer lumens as there are distal suture arms 50.

Figure 3A:
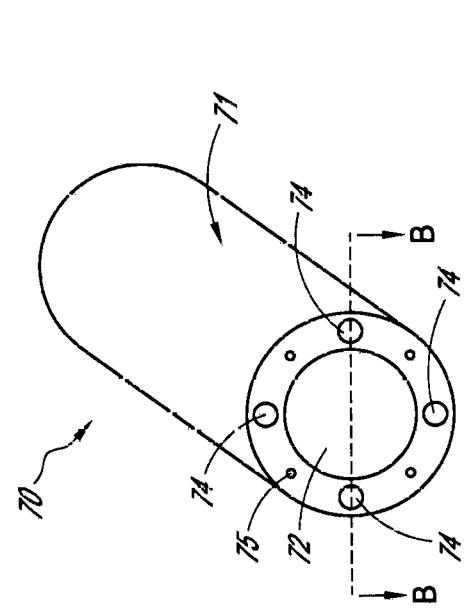
FIGS. 3A through 3D illustrate various embodiments of a needle carriage.

In some embodiments, as illustrated in FIG. 3A, the needle carriage 70 can have one or more sections, such as a first section 76A and a second section 76B. The first and second sections can be separated by one or more weakened areas 77 that allow the first section and second section to be broken apart and separated from each other so that the carriage can be removed from around the elongate body of a suturing device, as described below.

In some embodiments, the weakened area 77 can be a complete dislocation, such that the first section and second section are not integral. In some embodiments, a clasp or ring 78 can be used to maintain the first and second sections together until an operator decides to separate them. In some embodiments, the needle carriage can have a plurality of sections separated by weakened areas or complete dislocations.

Figure 3B:
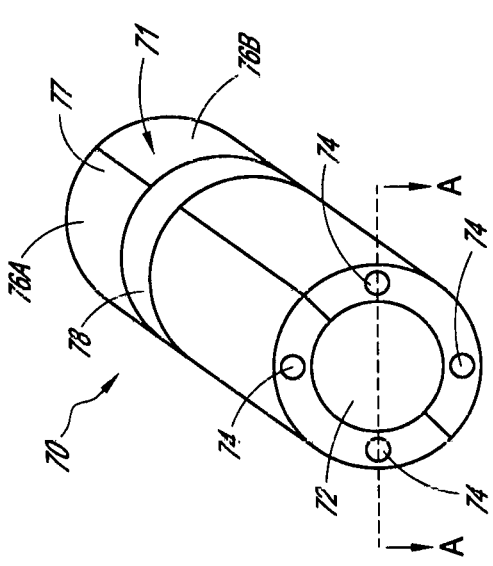
Figure 3C:
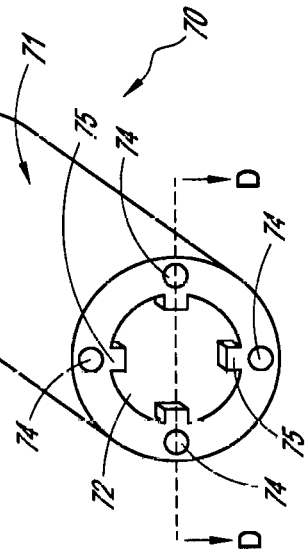

In some embodiments, as illustrated in FIG. 3B, the needle carriage 70 can include one or more keys or detents 75 along a distal facing surface. The detents can be used to help align the needle carriage with the proximal extensions or arms 60, as described in more detail below. In some embodiments, as illustrated in FIG. 3C, the needle carriage can include a spreader section 80 at a distal end. The spreader section can be used to help deflect needles exiting the outer lumens 74 such that they exit at a desired angle relative to a central axis of the needle carriage. In some embodiments, the spreader section can be a ring or other attachment connected to the body 71 of the needle carriage. In some embodiments, the spreader section can be integrally formed with and be part of the body 71 of the needle carriage.

Figure 3D:
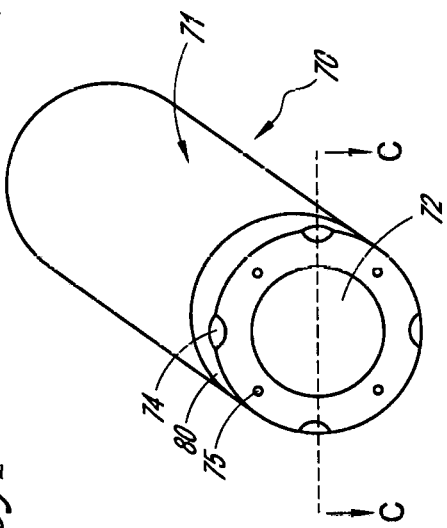

In some embodiments, as illustrated in FIG. 3D, a needle carriage 70 can include one or more keys or detents 50 that project into the central lumen 72. In some embodiments, keys or detents that project inward can interact with recesses on the elongate body to act as an index point, as described further below.

FIGS. 4A through 4D illustrate cross-sectional views of the embodiments illustrated in FIGS. 3A through 3D, respectively. FIGS. 4A through 4D illustrate a suture catch mechanism or needle 90 positioned within the outer lumens 74. The needles are illustrated in a retracted position within a corresponding outer lumen. In some embodiments, the needles can move to a deployed position in which a distal tip of the needle extends out of the lumen, as described in more detail below. FIG. 5C illustrates the spreader section 80. The spreader section can include a spreader ramp or angled face 82 that can be used to deflect the needles away from the needle carriage 70 when they move to a deployed position. As illustrated in FIG. 5D, in some embodiments a key or detent 75 extends into the central lumen 72 of the needle carriage 70. In some embodiments, the key 75 can have an angled or beveled surface 73. The angled surface can help the key 75 move out of a corresponding recess on the elongate body, as described further below.

Figure 5:
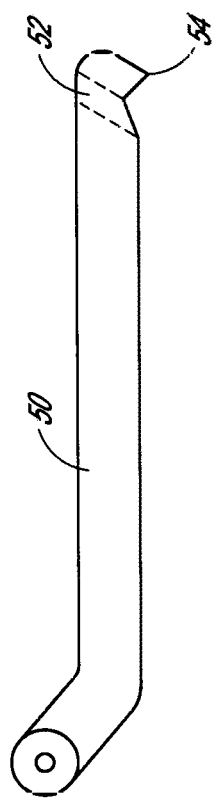
FIG. 5 is a schematic drawing of one embodiment of a distal arm.

FIG. 5 illustrates one embodiment of a distal suture arm 50. As described above, the suture arm can include a suture mount or clasp 52 that can releasably retain a suture portion (not illustrated). The suture clasp can include an opening that extends through the arm, which allows a suture catch mechanism or needle to pass through the opening when extended and then catch the suture when retracted, drawing the suture with it. As illustrated, in some embodiments a distal suture arm can include a sharp edge 54, or any hook point needle tip knurling or other roughening on a surface that faces towards a proximal end of the elongate body when the suture arm is in the extended position. A sharp edge or other roughening can help retain the suture arm in a position against body tissue, as described below.

Figure 6A:
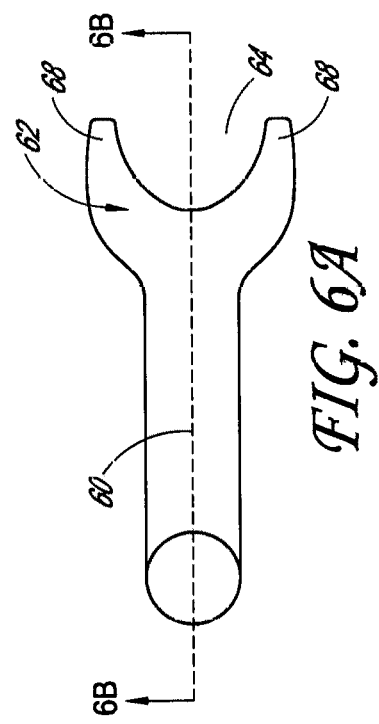
FIG. 6A is a schematic drawing of one embodiment of a proximal arm.
Figure 6B:
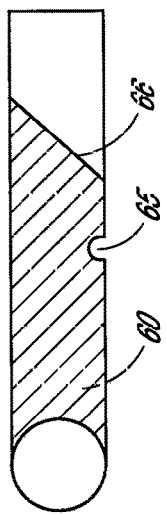
FIG. 6B is a cross-sectional view taken along the line 6B-6B of the embodiment of FIG. 6A.

FIGS. 6A and 6B illustrate one embodiment of a proximal extension or arm 60. FIG. 6A illustrates a top view of the arm and FIG. 6B illustrates a cross-section of the arm along the line 6B-6B of FIG. 6A. In some embodiments, a proximal arm can include a needle receiving end 62 that has a needle receiving or needle guiding section 64. The needle receiving end can include one or more extensions 68 that at least partially surround the needle guiding section, limiting the lateral motion of a needle passing through the needle guiding section.

In some embodiments, a proximal extension or arm 60 can include a spreader ramp or angled surface 66. This can be used to help deflect a needle through the needle guiding section 64 and toward a suture mount or clasp of a distal arm. Also as illustrated in FIG. 6B, in some embodiments a proximal arm 60 can include a detent mating recess 65, which can be used to mate with a detent 75 of a needle carriage 70, ensuring alignment between the outer lumens 74 and the needle guiding section 64. In some embodiments, the arm can include a protruding detent, and the needle carriage can have one or more corresponding detent mating recesses. In some embodiments, engagement of the protruding and recessed detents can indicate to an operator of the device that the needle carriage is in a desired position relative to the elongate body 40.

In some embodiments, the elongate body 40 of a suturing device can have one or more key or detent recesses 45 instead of or in addition to proximal extensions or arms. In some embodiments, each of the key recesses can be configured to mate with a corresponding key projection on a needle carriage.

Figure 7:
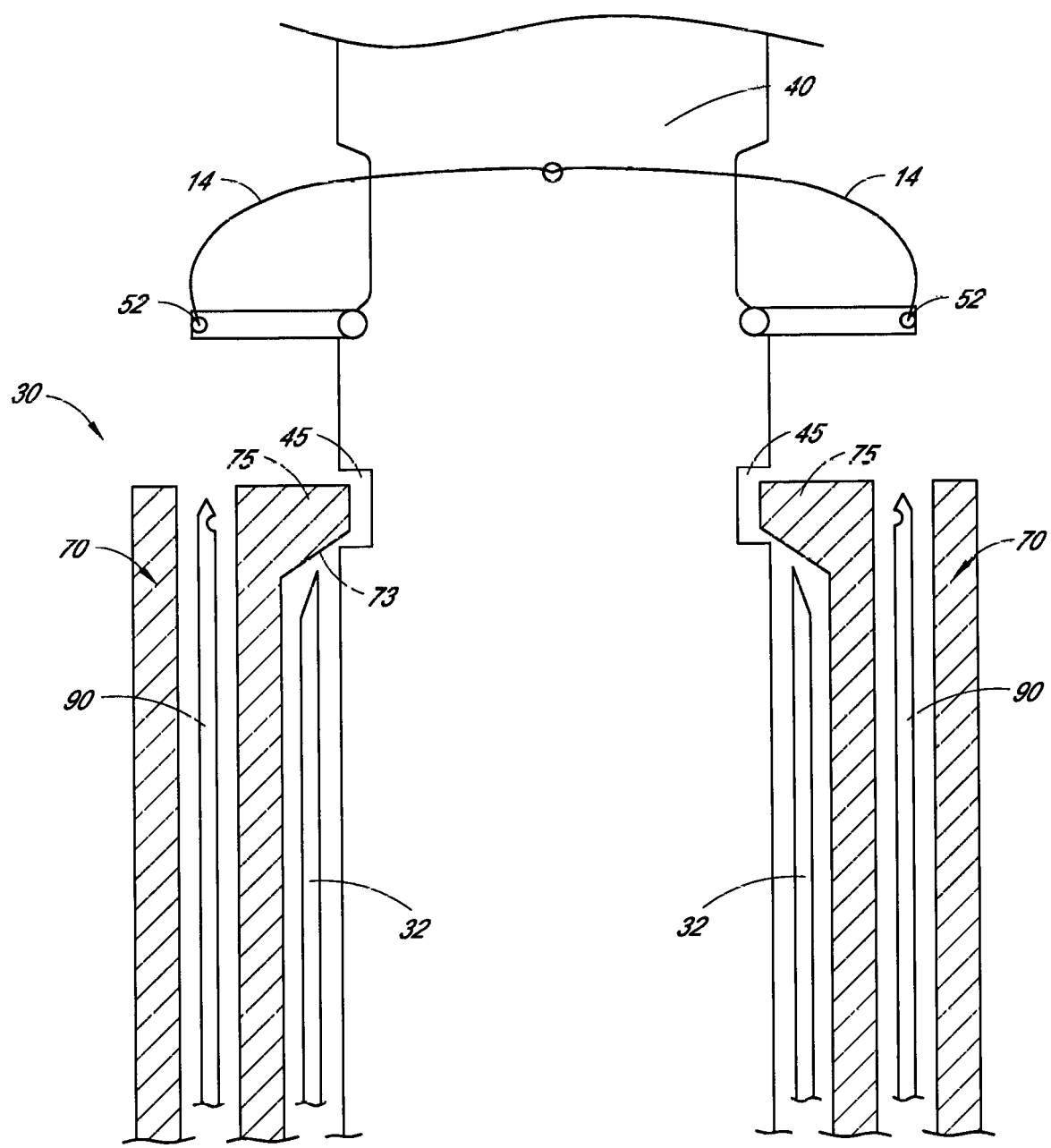
FIG. 7 is a schematic cross-sectional view of one embodiment of a section of a suturing system distal assembly.
Figure 8:
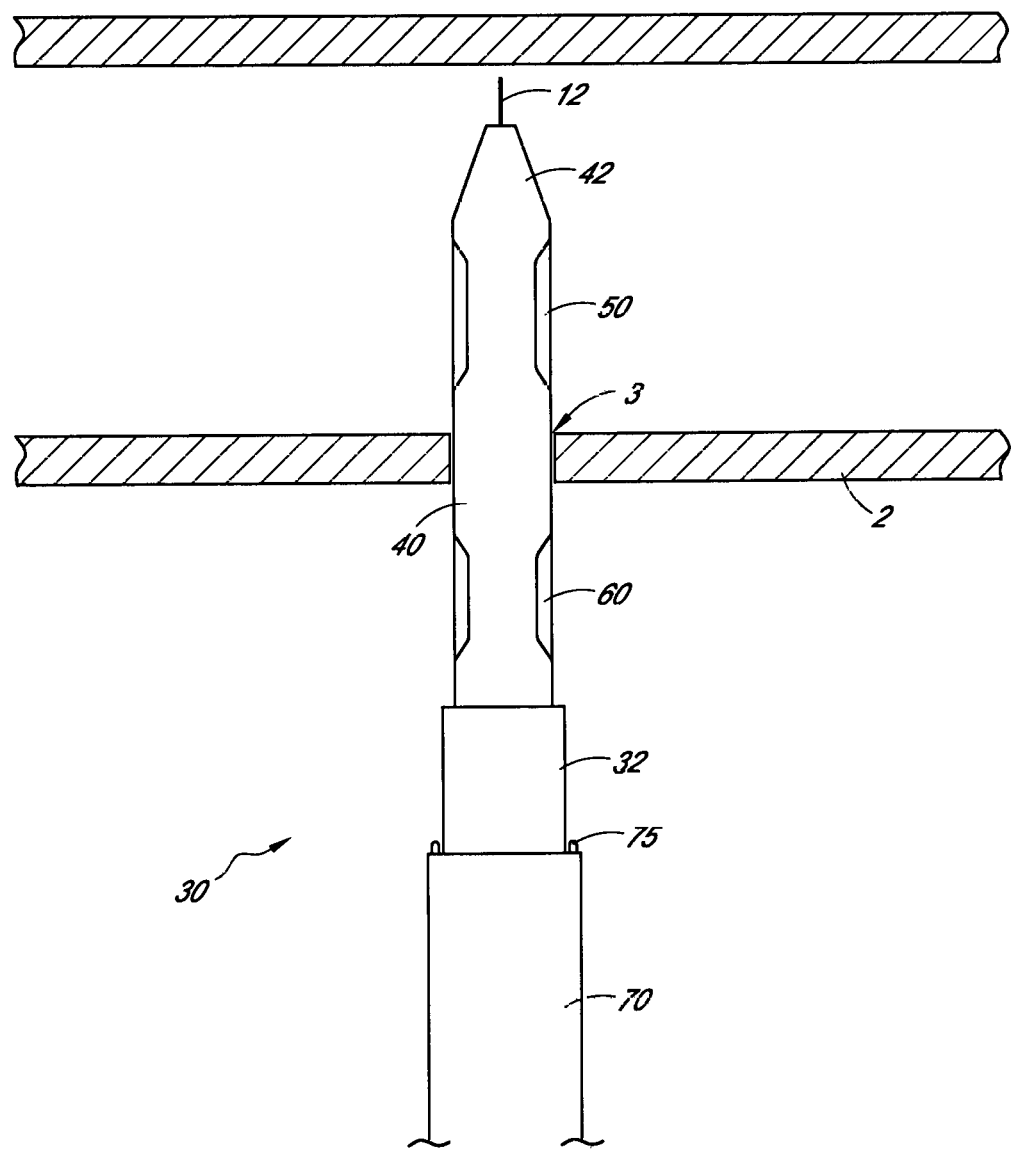
FIG. 8 is a schematic representation of a suturing system passing through an opening in an aorta wall.

FIG. 7 illustrates a schematic cross-sectional view of a portion of a distal assembly 30 that has a plurality of key recesses instead of proximal extensions to help identify when the needle carriage is in a desired position relative to the elongate body 40. As illustrated, the detents 75 can fit into the recesses 45. In some embodiments, the needle carriage 70 can be biased into the illustrated position but can flex outward. In such embodiments, when moving the needle carriage proximally from the illustrated position, the angled surface 73 on the detent 75 can contact a corner of the recess 45, which pushes the detent outward, allowing the carriage to be retracted. Additionally, when the sheath 32 is moved distally relative to the carriage 70, the sheath can contact the angled surface 73 and flex the needle carriage outward, allowing the sheath to pass the detent 75.

In some embodiments, as further illustrated in FIG. 7, needles 90 can be longitudinally aligned with suture clasps 52. In some embodiments, the needle can be in longitudinal alignment with a position medial to the suture clasps 52, and the needle carriage can include a spreader section, as described above. FIG. 7 also illustrates an embodiment in which suture portions 14 extend outward from the elongate body 40 and loop into position with their distal ends in the suture clasps 52.

FIGS. 8 through 17 illustrate one method of using a suturing device 10 to place sutures through tissue near an opening 3 in a biological structure, such as the aorta 2. The device can further be used to position a sheath through the opening to allow for entry of other devices, while maintaining or nearly maintaining hemostasis. In the illustrated method a suturing device 10 is inserted into the chest cavity through a trocar in the chest wall to access the aorta, though as discussed above the suturing device can be used with a variety of other biological structures. The device 10 can follow a guidewire 12 through a puncture in the aortic wall 2, the tapered distal end 42 widening the opening 3 as the device enters further into the aorta. The device is preferably inserted until the distal suture arms 50 have completely passed through the hole 3 in the wall 2 and are completely within the aorta.

Figure 9:
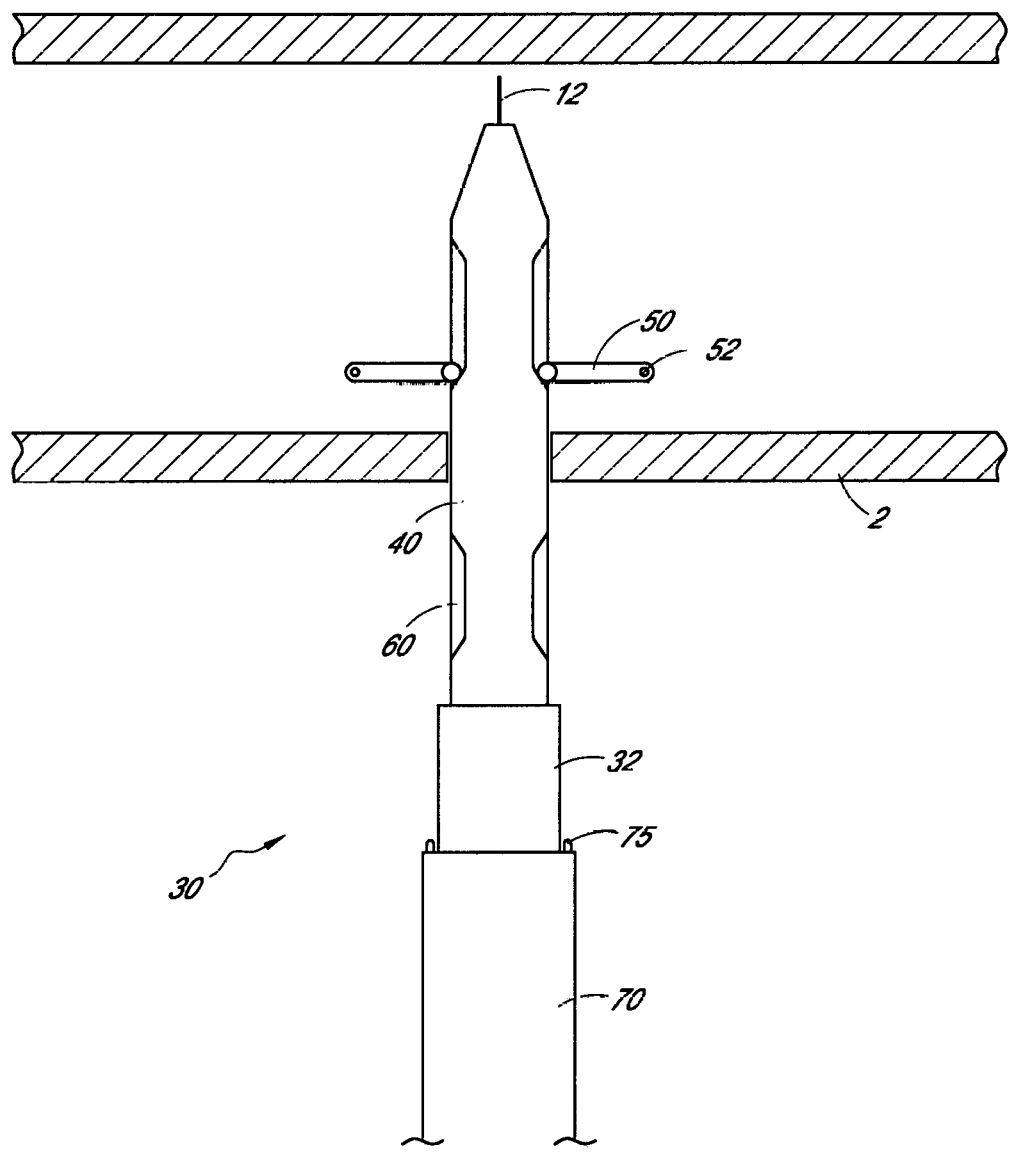
FIG. 9 is a schematic representation as in FIG. 8 showing distal arms in an extended position.
Figure 10:
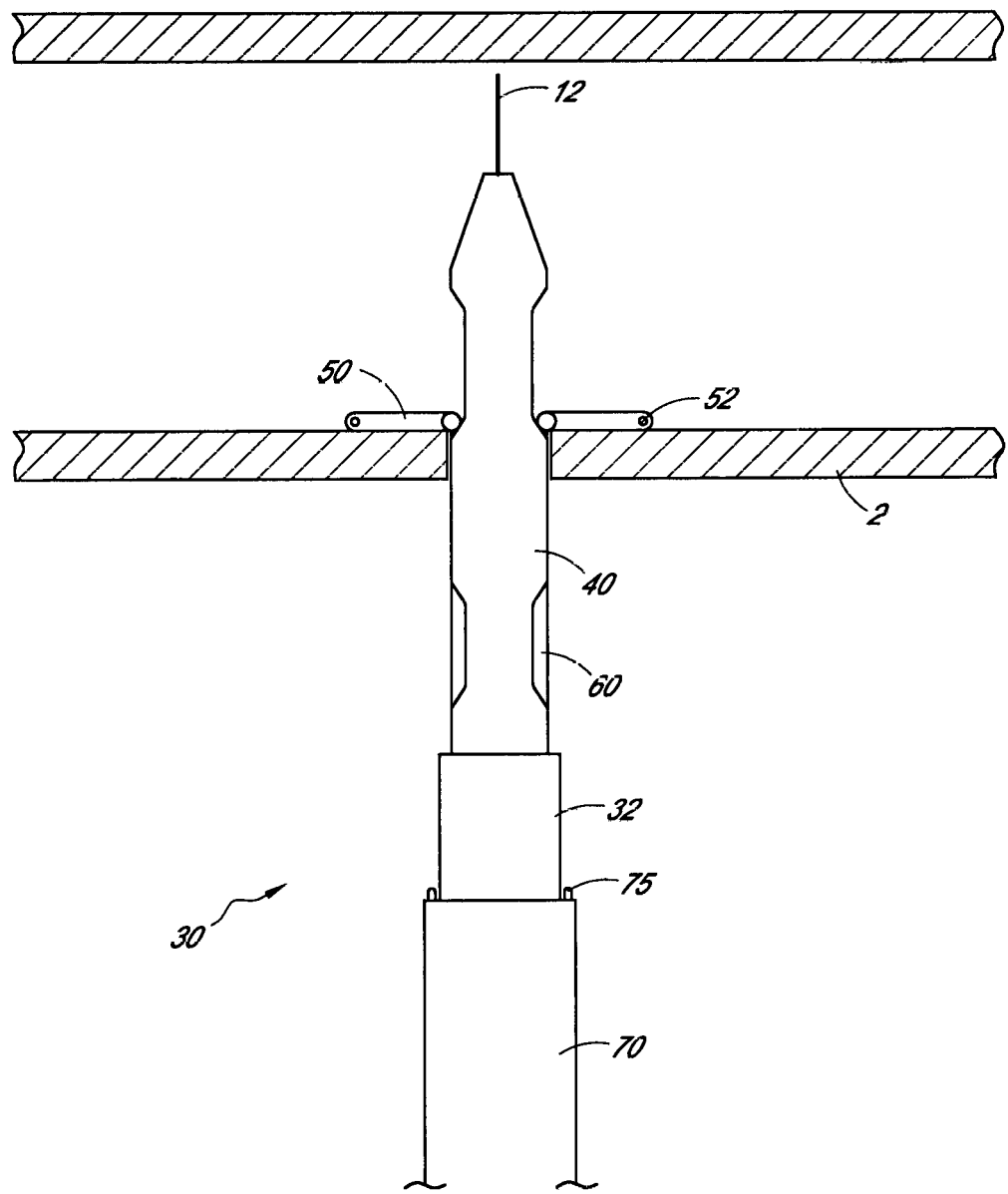
FIG. 10 is a schematic representation as in FIG. 9 showing distal arms in contact with the aorta wall.
Figure 11:
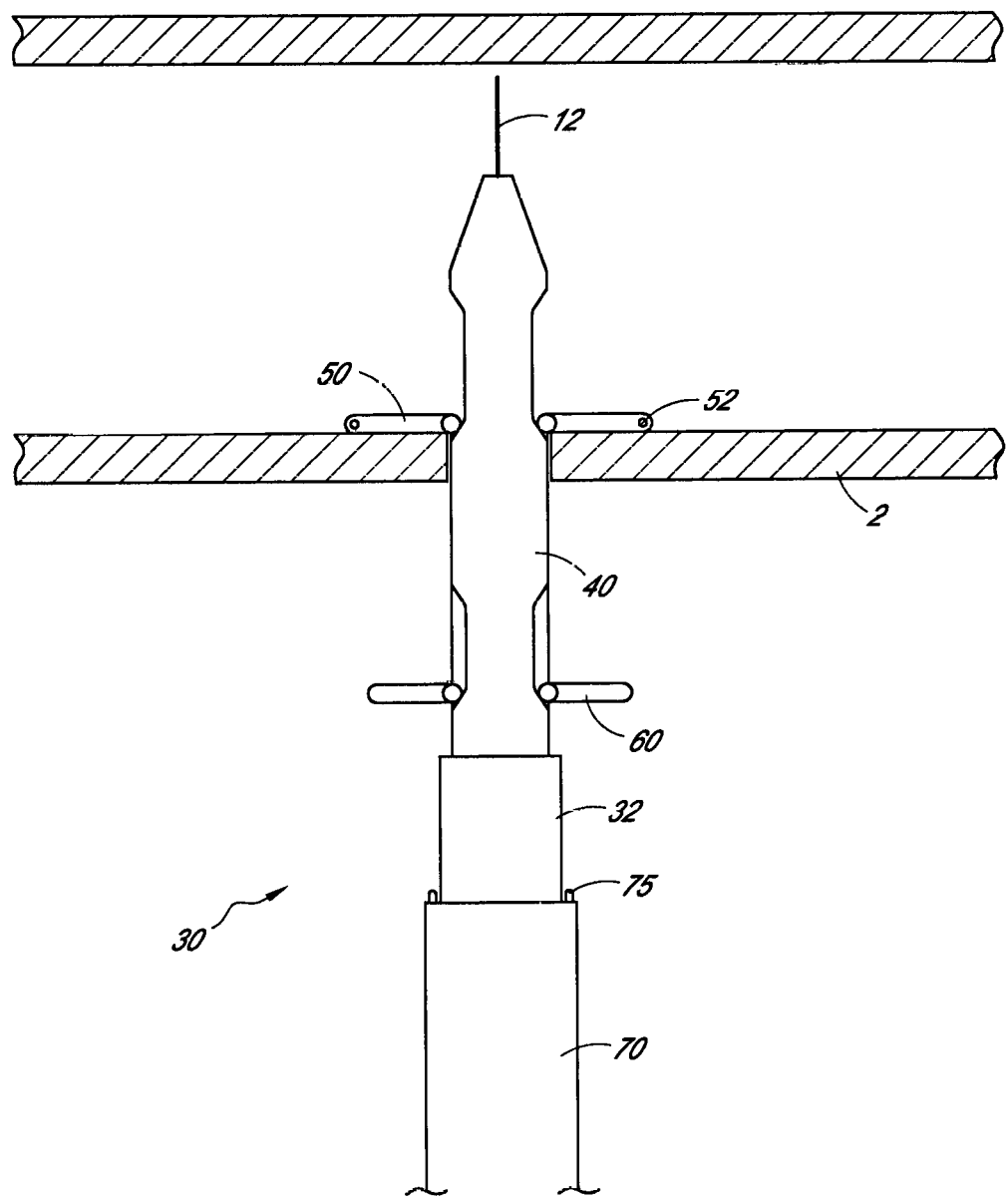
FIG. 11 is a schematic representation as in FIG. 10 showing proximal arms in an extended position.

As illustrated in FIG. 9, once the distal arms 50 are completely within the aorta they can be moved into the extended position. An operator of the device can then withdraw the device until the arms contact the aortic wall 2, as illustrated in FIG. 10. In some embodiments, a sharp edge or roughening in the suture arms 50, as described above, can help maintain the distal assembly 30 in position. In FIG. 11, the proximal arms 60 have been moved into an extended position within the chest cavity, and the device now has both sets of arms in the extended position with the distal arms braced against the aortic wall 2. As discussed above, the distal and proximal arms are preferably in alignment.

Figure 12:
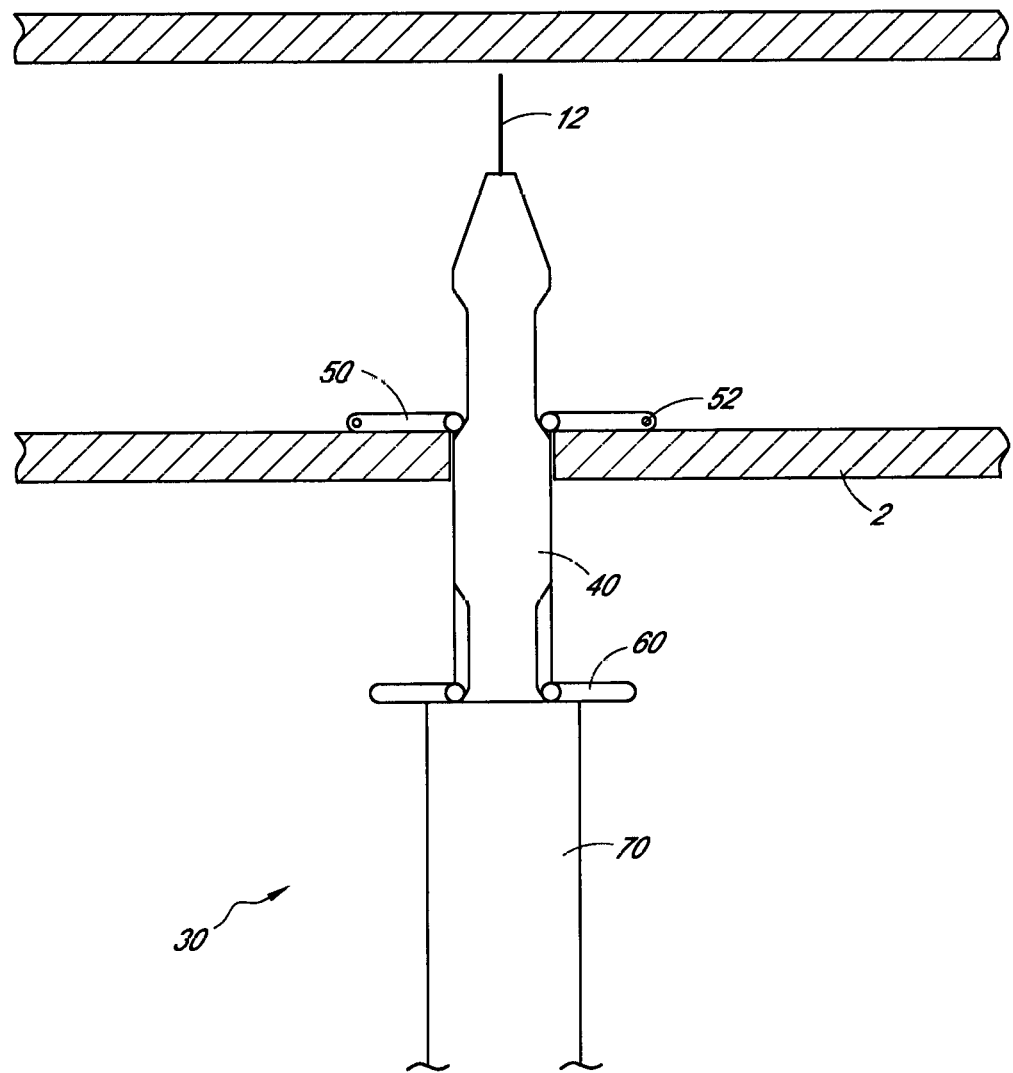
FIG. 12 is a schematic representation as in FIG. 11 showing a needle carriage advanced into a position adjacent the proximal arms.

Once the proximal arms 60 have been extended, the needle carriage 70 can be advanced until it contacts or is adjacent the proximal arms 60, as illustrated in FIG. 12. In some embodiments, the proximal arms 60 can serve as an index point, and an operator of the device can rely upon contact with the proximal arms to indicate that the needle carriage has advanced to a desired position along the length of the elongate body 40. As described above, in some embodiments the needle carriage and proximal arms can have corresponding detents which can help ensure that the needle carriage is properly aligned circumferentially relative to the proximal arms. Where the proximal and distal arms 50 are aligned, aligning the needle carriage with the proximal arms also aligns the needle carriage with the distal arms. In some embodiments, other alignment mechanisms can be used to ensure proper alignment. In some embodiments, the outer lumens of needle carriage can each be aligned with a corresponding proximal arm and a corresponding distal arm.

Figure 13A:
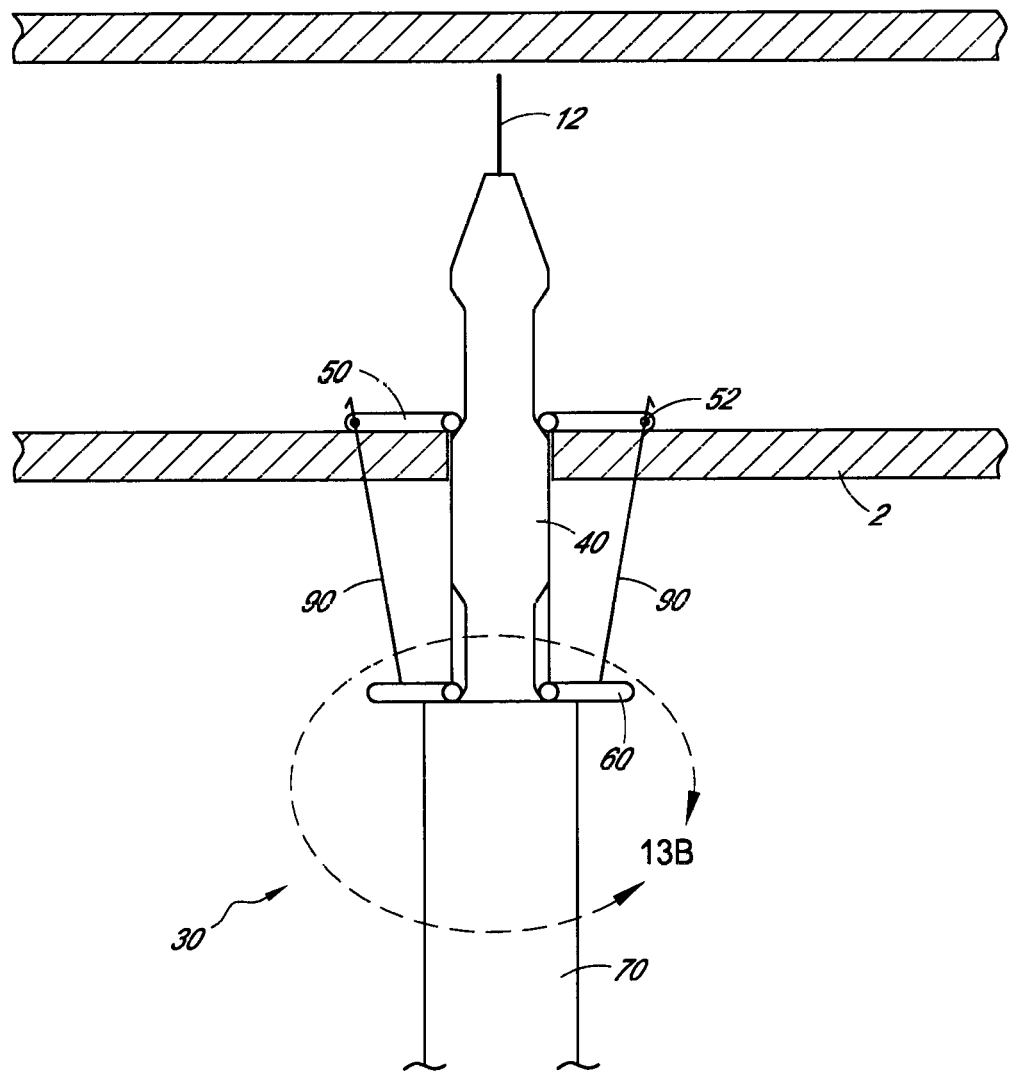
FIG. 13A is a schematic representation as in FIG. 12 showing suture catch mechanisms engaging suture clasps.

As illustrated in FIG. 13A, once the needle carriage 70 is positioned against or near the proximal arms 60 and aligned as desired, the needles 90 can be extended from a retracted position in which the needles are within the needle carriage and a distal point of the needles is proximal to the proximal arms, to a deployed position in which a distal point of the needles extends out from the needle carriage and into a corresponding suture mount. As illustrated, the needles in the deployed position must pass through the aortic wall 2 to reach a corresponding suture mount or clasp 52.

As described above, the needle carriage can include a spreader or deflector section that can deflect the needles at an angle outward from a longitudinal axis of the needle carriage and elongate body. In some embodiments, rather than having a spreader section in the needle carriage, the proximal arms 60 can include a spreader ramp or angled surface 66 that can be used to deflect the needles outward, as discussed above. In some embodiments, both the needle carriage 70 and proximal arms 60 can have a spreader ramp or angled surface that can help deflect the needles when the needles move from a retracted to a deployed position.

Figure 13B:
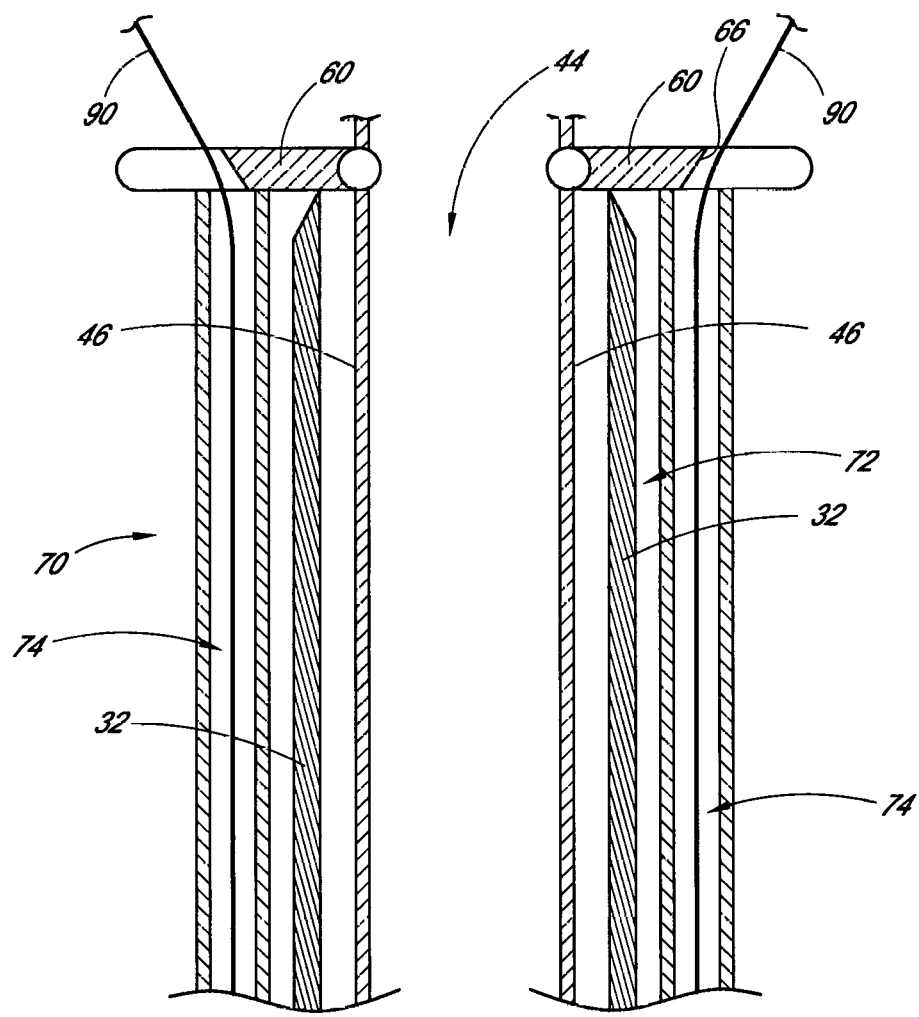
FIG. 13B is a cross-sectional view of the section identified as 13B in FIG. 13A.

To provide a clearer illustration of the relationship between various components of the distal assembly 30 in the illustrated embodiment, FIG. 13B illustrates a cross-sectional view of the section identified as 13B in FIG. 13A. As illustrated, the suture catch mechanism or needles 90 are in a deployed position, extending out of the outer lumens 74 of the needle carriage 70. A spreader ramp or angled surface 66 on the proximal arms 60 has deflected the needles away from the elongate body and from the needle carriage. Within the central lumen 72 of the needle carriage 70 is the sheath 32 and walls 46 of the elongate body.

Figure 14:
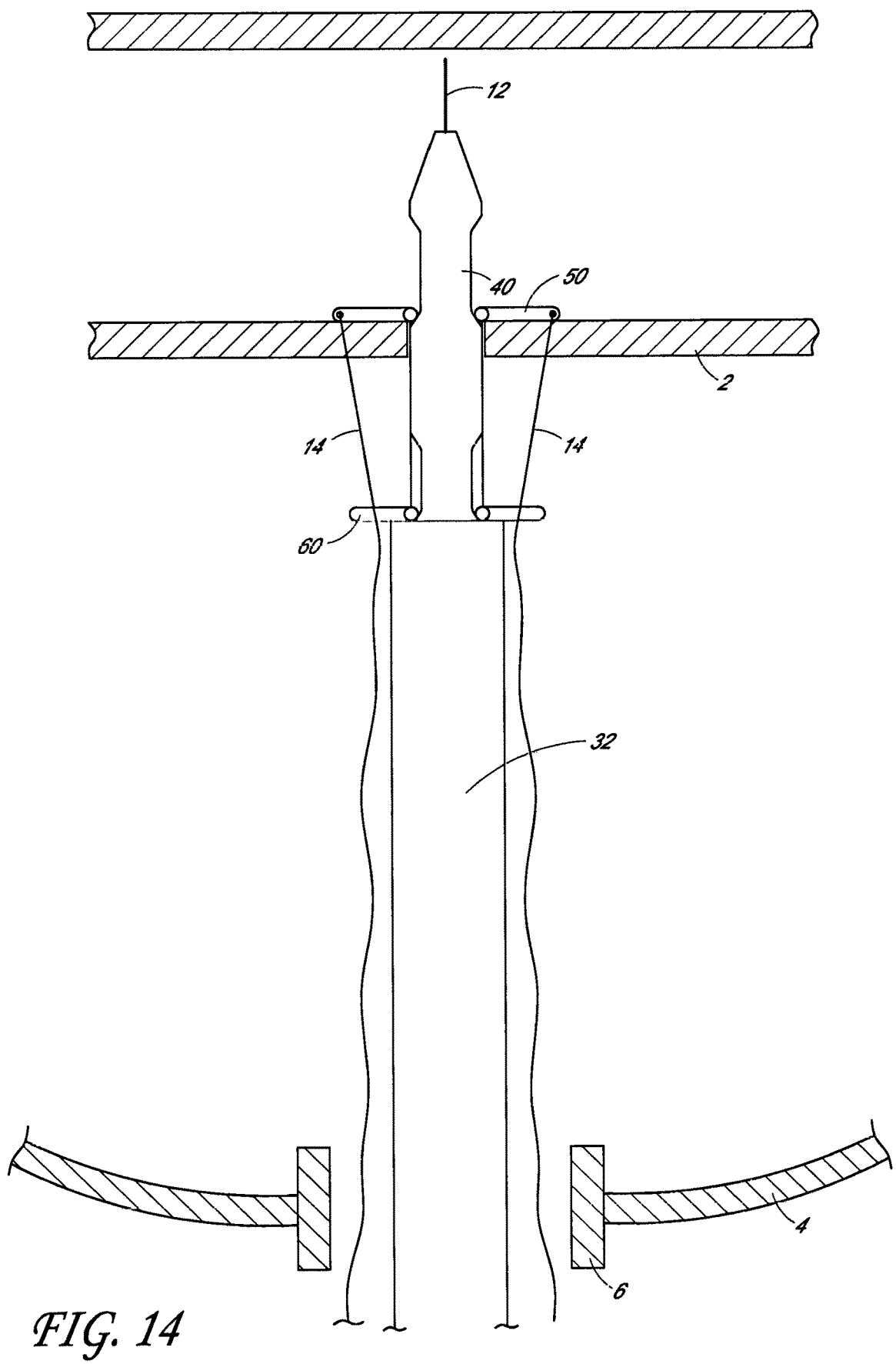
FIG. 14 is a schematic representation as in FIG. 13A showing the needle carriage withdrawn and suture ends passing through a trocar inserted into a chest wall.

The needles in the deployed position can engage the sutures 14, releasably positioned in the suture clasps 52, such that when the needles retract back into the needle carriage they draw the suture ends with them, as illustrated in FIG. 14. In some embodiments, the needles can move from the retracted to deployed (and from the deployed to the retracted) position simultaneously. In some embodiments, the needles can move sequentially between positions. In some embodiments, the needle carriage may have only a single needle that catches a suture end from a first suture clasp, rotates with the needle carriage into alignment with a second suture clasp, and then catches a suture end from the second suture clasp.

Once the needles have fired and drawn sutures through the aortic wall 2, the needle carriage can be withdrawn from within the chest cavity, drawing the suture ends with it. As illustrated in FIG. 14, the ends of suture captured by the needles will run from within the elongate body 40, through the aortic wall 2, and then out of the body cavity, such as through a trocar 6 through the chest wall 4. Once the needles have been withdrawn, the needle carriage can be moved to a position that is out of the way. In some embodiments, this can include moving the needle carriage proximally out of the body cavity. In some embodiments, the needle carriage can be separated into different sections, as described above, and removed entirely from around the elongate body.

Figure 15:
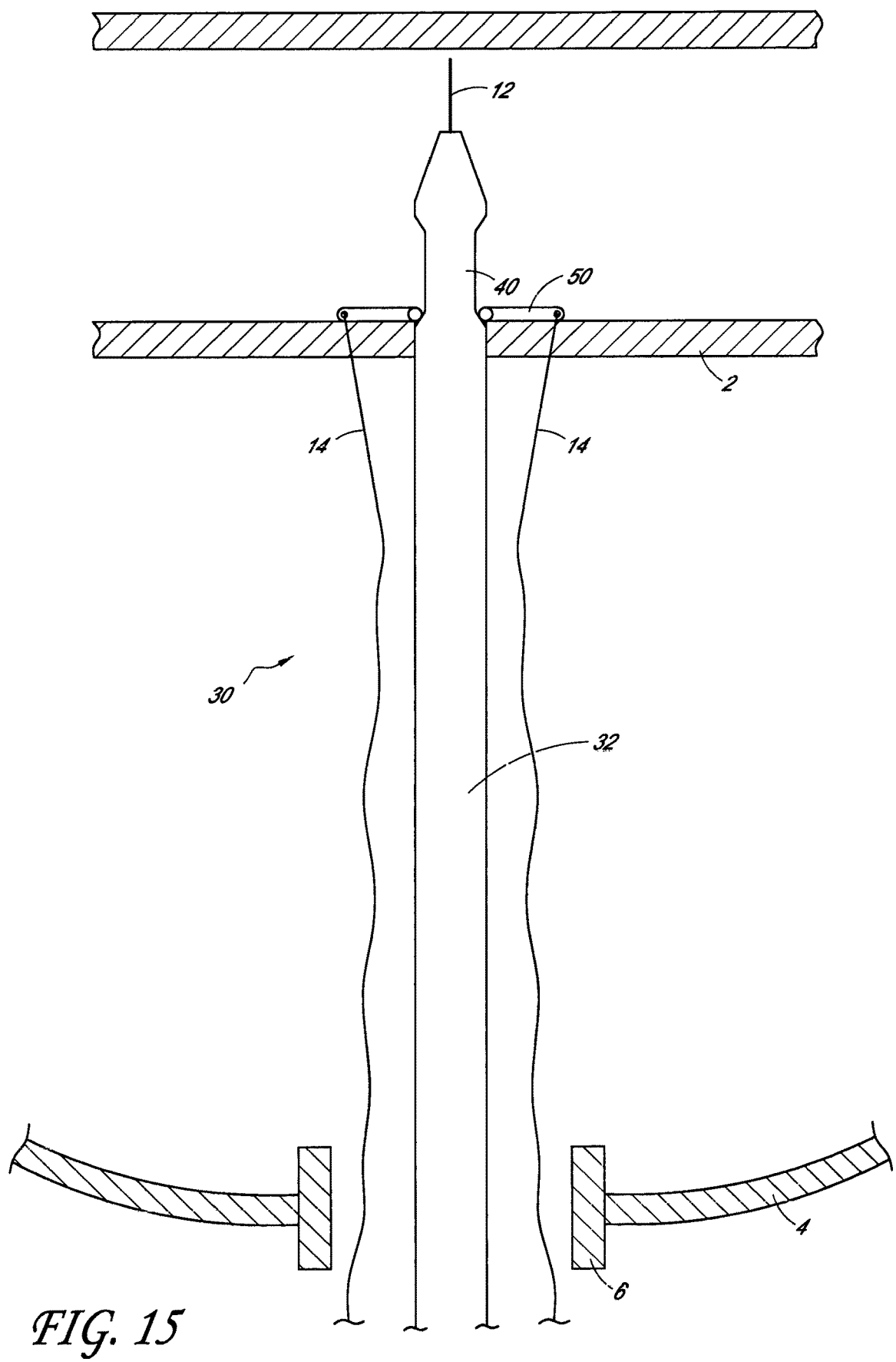
FIG. 15 is a schematic representation as in FIG. 14 showing a sheath advanced into the hole in the aorta wall.
Figure 16:
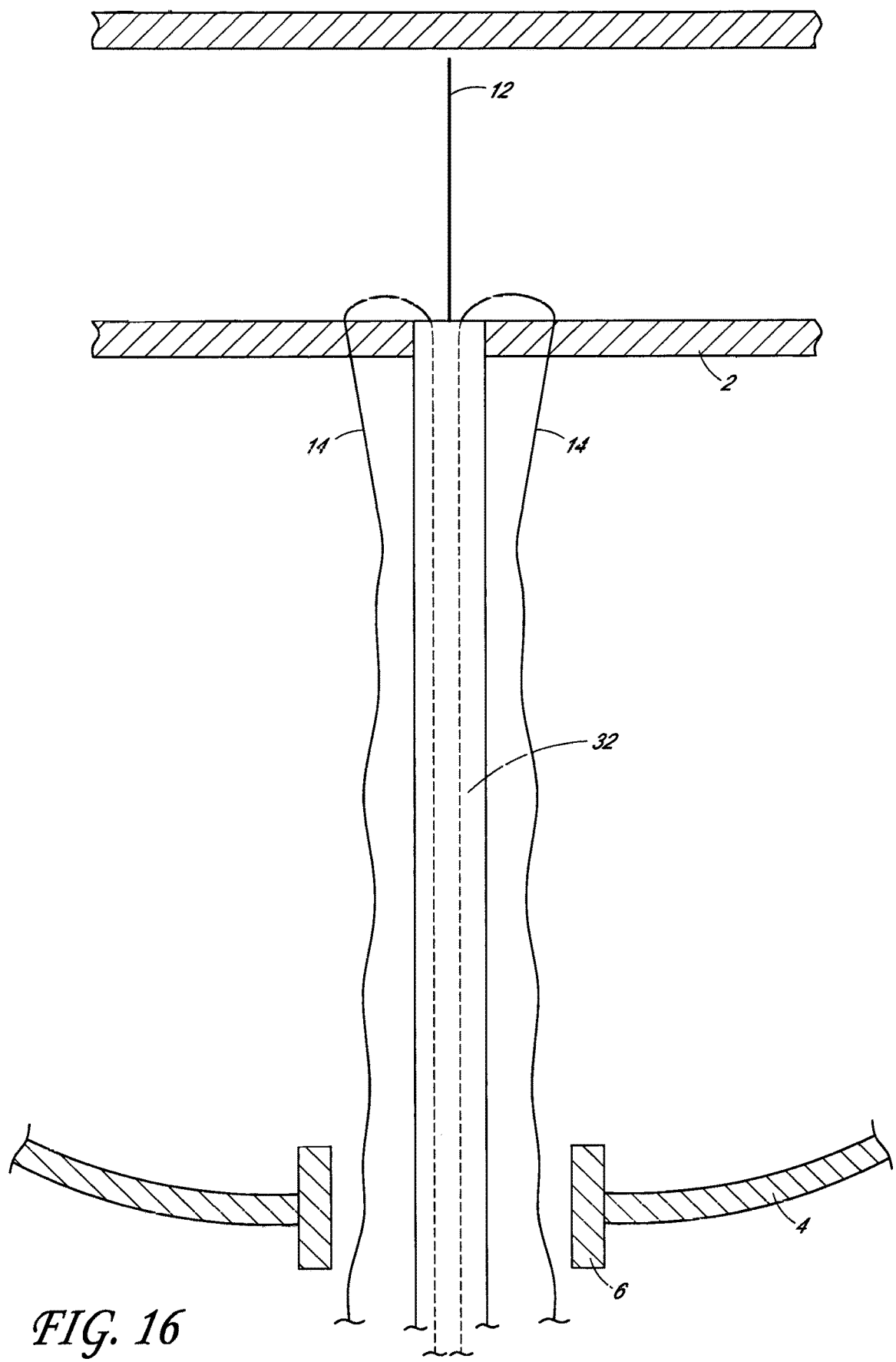
FIG. 16 is a schematic representation as in FIG. 15 showing the device withdrawn and the sheath remaining in the hole in the aorta wall.

As illustrated in FIG. 15, the proximal arms 60 can be moved back into a retracted position and the sheath 32 can be advanced distally through the hole in the aortic wall 2. Preferably, the sheath is advanced until it contacts the distal suture arms 50, thus providing an operator with confirmation that the sheath is within the hole in the aortic wall. Once the sheath is within the hole, the sheath can be relied upon to maintain hemostasis, the distal arms 50 can be returned to a retracted position, and the suturing device can be removed from within the sheath, as illustrated in FIG. 16. Thus, the suture portions 14 that were within the suturing device will pass through the sheath and out of the body cavity, and the remaining suture will pass as previously illustrated as described.

Figure 17:
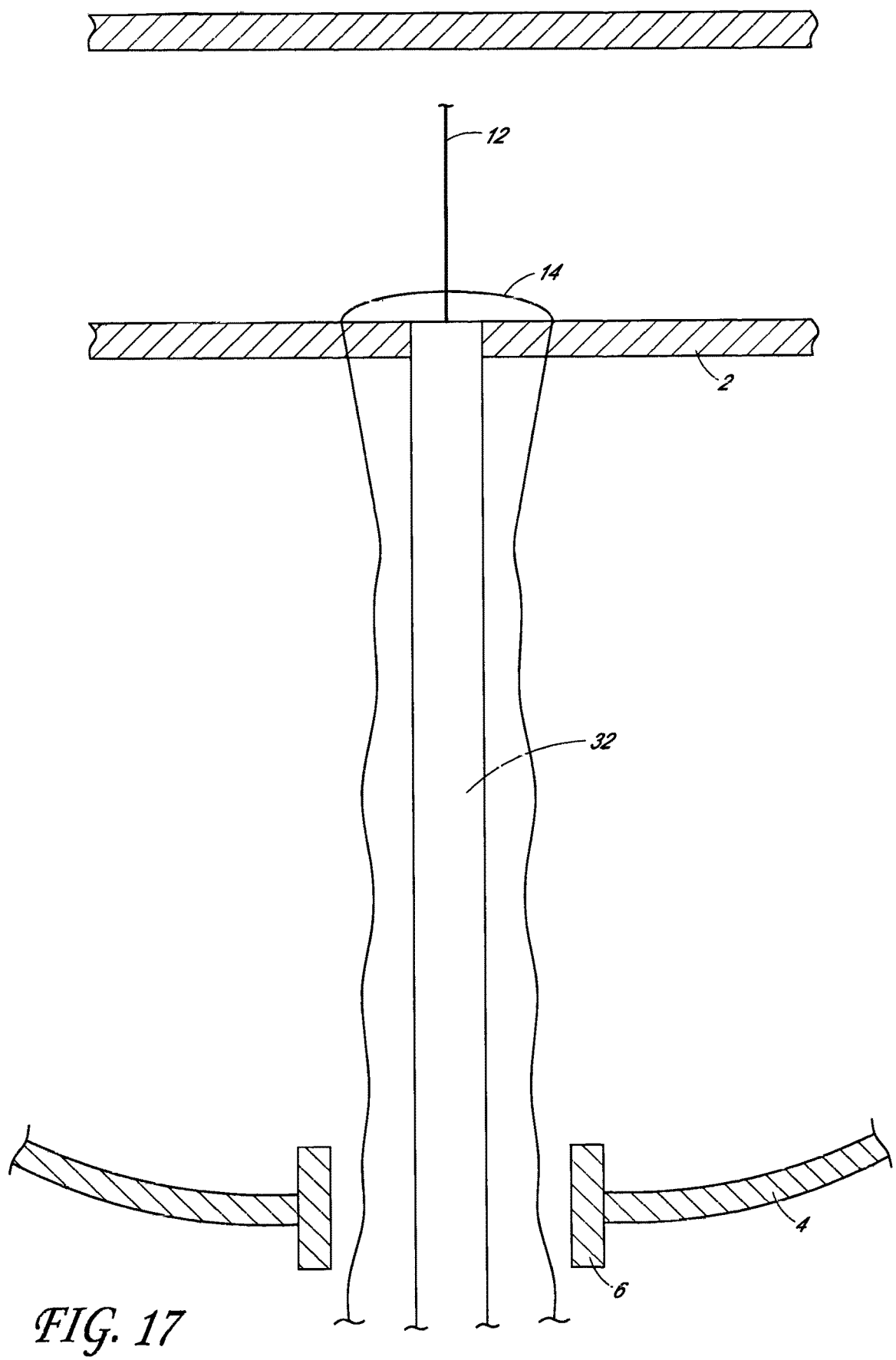
FIG. 17 is a schematic representation as in FIG. 16 showing a suture portion pulled into the aorta.

In some embodiments, suture arms 60 that are positioned approximately 180 degrees apart from each other can be preloaded with a single piece of suture. In such embodiments, when the device is removed from the sheath 32, the suture portions extending through the sheath are joined together and the only ends of suture extend outside of the sheath. The ends extending outside of the sheath can be pulled, and the joined suture portions can be pulled through the sheath and into the vessel as illustrated in FIG. 17.

In some embodiments, if a single piece of suture is not used and the suture portions passing through the sheath need to be secured together, they can be secured together with a knot or other device prior to pulling on the ends of suture passing outside of the sheath. Further details regarding a device for joining sutures are provided in U.S. Patent Application Publication No. 2011/0190793, published on Aug. 4, 2011, which is hereby incorporated by reference herein in its entirety and a copy of which is enclosed and is included as part of this specification.

In some embodiments, suture ends that pass through the sheath can be secured together in pairs, each pair having suture ends that had been releasably attached to arms 50 spaced about 180 degrees apart around the circumference of the elongate body 40. By then pulling on one or more of the remaining free suture ends, the joined suture 14 can be pulled through the sheath and into the blood vessel, as illustrated in FIG. 17. FIG. 17 only shows one suture, but other sutures can pass in planes other than the illustrated plane. In some embodiments, a second suture can pass through the aorta in a plane substantially perpendicular to the illustrated cross-section.

Further details regarding procedures for tying sutures and methods for closing openings can be found in PCT Application No. PCT/US2013/040418, filed on May 9, 2013, which is hereby incorporated by reference herein in its entirety and a copy of which is enclosed and is included as part of this specification.

Once the suture 14 has been pulled into the aorta as illustrated in FIG. 17, a suturing or other surgical device can be inserted through the sheath 32 and into the aorta. In some embodiments, prior to inserting a device into the aorta, it may be desirable to replace the sheath with a different sheath. This can be done by standard procedures known in the art, and can also be done while maintaining a sheath within the opening to thereby maintain hemostasis. For example, an obturator may be slid over the sheath 32. The sheath 32 can then be removed, and a larger sheath may be delivered over the obturator.

Once the desired procedure or procedures have been performed, the sheath can be withdrawn while tightening the sutures to close the opening around the sheath as the sheath is withdrawn. In some embodiments, a tapered sheath can be inserted prior to closing the opening, which can make it easier to close the opening tightly around the sheath as the sheath is withdrawn from the aorta. In some embodiments, a knot delivery device, such as the device mentioned above and described in U.S. Patent Application Publication No. 2011/0190793 and incorporated by reference herein, can be preloaded with two or more of the end portions of sutures 14 and delivered into the body cavity alongside the sheath, making it easier to maintain a tightening pressure as the sheath is withdrawn. The opening in the aorta wall can then be closed by applying or tying a knot to the suture ends or by other known methods.

Although the foregoing description of the preferred embodiments has shown, described and pointed out the fundamental novel features of the invention, it will be understood that various omissions, substitutions, and changes in the form of the detail of the apparatus as illustrated as well as the uses thereof, may be made by those skilled in the art, without departing from the spirit of the invention.

Reference throughout this specification to "one embodiment" or "an embodiment" means that a particular feature, structure or characteristic described in connection with the embodiment is included in at least one embodiment. Thus, appearances of the phrases "in one embodiment" or "in an embodiment" in various places throughout this specification are not necessarily all referring to the same embodiment. Furthermore, the particular features, structures or characteristics of any embodiment described above may be combined in any suitable manner, as would be apparent to one of ordinary skill in the art from this disclosure, in one or more embodiments.

Similarly, it should be appreciated that in the above description of embodiments, various features of the inventions are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Rather, as the following claims reflect, inventive aspects lie in a combination of fewer than all features of any single foregoing disclosed embodiment. Thus, the claims following the Detailed Description are hereby expressly incorporated into this Detailed Description, with each claim standing on its own as a separate embodiment.

What is claimed is:

1. A suturing system, comprising:
    a suturing device comprising an elongate body having a proximal end and a distal end;
    a first plurality of arms near the distal end, wherein each arm of the first plurality of arms comprises a fixed end and a free end, and is configured to rotatably move between a first position wherein the arm is retracted within the elongate body and the fixed end is located proximal to the free end, and a second position wherein the free end extends away from the elongate body, the fixed end coupled to the elongate body opposite the free end when in the first position and in the second position, and each arm comprising at least one suture mount at the free end;
    a second plurality of arms proximal to the first plurality of arms, wherein each arm of the second plurality of arms is configured to move between a first position wherein the arm is retracted within the elongate body, and a second position wherein the arm has a free end extending away from the elongate body, each of the second plurality of arms having a length extending from an end coupled to the elongate body to the free end, and a width that is transverse to the length;
    a sheath adapted to surround at least a portion of the elongate body;
    a plurality of needles, each needle configured to move between a retracted position in which a distal point of the needle is proximal to the second plurality of arms and a deployed position in which the distal point of the needle extends through an arm of the second plurality of arms and into a corresponding suture mount of the first plurality of arms, wherein each of the second plurality of arms comprises a needle guide path that extends across the width of each of the second plurality of arms; and
    a plurality of suture portions, wherein each suture portion has a suture end releasably retained within the suture mount of a corresponding arm of the first plurality of arms.

2. The suturing system of claim 1, wherein the first plurality of arms comprises four arms near the distal end.

3. The suturing system of claim 2, wherein the suturing device comprises four needles, each needle associated with a corresponding arm of the first plurality of arms.

4. The suturing system of claim 2, wherein the second plurality of arms comprises four arms, each of the second plurality of arms aligned with a corresponding arm of the first plurality of arms.

5. The suturing system of claim 1, wherein the needles are configured to simultaneously move to the deployed position.

6. The suturing system of claim 1, wherein the free ends of the each of the first plurality of arms move proximally when the arms move from the first position to the second position.

7. The suturing system of claim 1, further comprising a needle carriage configured to at least partially surround the elongate body.

8. The suturing system of claim 7, wherein the needle carriage is configured to at least partially surround at least a portion of the sheath.

9. The suturing system of claim 7, wherein the needle carriage comprises at least two separable pieces.

10. The suturing system of claim 7, wherein the needle carriage comprises a plurality of lumens.

11. The suturing system of claim 10, wherein each of the plurality of needles is positioned within a lumen of the plurality of lumens.

12. The suturing system of claim 7, wherein the needle carriage comprises at least one detent at a distal end configured to mate with a detent on a proximal surface of an arm of the second plurality of arms.

13. The suturing system of claim 12, wherein the needle carriage detent is a protrusion and the arm detent is a recess.

14. The suturing system of claim 1, wherein each of the second plurality of arms are shorter than each of the first plurality of arms so that when in the second position, the free end of each of the first plurality of arms is further away from the elongate body than the free end of each of the second plurality of arms.

15. The suturing system of claim 1, wherein the first plurality of arms are substantially parallel to the second plurality of arms in the second position.

16. The suturing system of claim 1, wherein the second plurality of arms in the second position are at 90 degrees to the elongate body.

17. The suturing system of claim 1, wherein the needle guide path comprises a ramp or angled surface.

18. The suturing system of claim 1, wherein the needle guide path is located at or near the free end of an arm of the second plurality of arms.

19. A suturing system, comprising:
a suturing device comprising an elongate body having a proximal end and a distal end;
a first plurality of arms near the distal end, wherein each arm of the first plurality of arms comprises a fixed end and a free end, and is configured to move between a first position wherein the arm is retracted within the elongate body and the fixed end is located proximal to the free end in the first position, and a second position wherein the free end extends away from the elongate body, the fixed end coupled to the elongate body opposite the free end when in the first position and in the second position, the free end rotating away from the elongate body when the arm moves from the first position to the second position, each arm comprising at least one suture mount at the free end;
a second plurality of arms proximal to the first plurality of arms, wherein each arm of the second plurality of arms is configured to move between a first position wherein the arm is retracted within the elongate body, and a second position wherein the arm has a free end extending away from the elongate body;
a sheath adapted to surround at least a portion of the elongate body;
a plurality of needles, each needle configured to move between a retracted position in which a distal point of the needle is proximal to the second plurality of arms and a deployed position in which the distal point of the needle extends through an arm of the second plurality of arms and into a corresponding suture mount;
a plurality of suture portions, wherein each suture portion has a suture end releasably retained within a suture mount of a corresponding arm of the first plurality of arms; and
a needle carriage configured to at least partially surround the elongate body, wherein the needle carriage comprises at least one detent at a distal end configured to mate with a detent on a proximal surface of an arm of the second plurality of arms.

20. The suturing system of claim 13, wherein the at least one detent on the needle carriage is a protrusion and the detent on the arm of the second plurality of arms is a recess.

21. A suturing system, comprising:
a suturing device comprising an elongate body having a proximal end and a distal end;
a first plurality of arms near the distal end, wherein each arm of the first plurality of arms comprises a fixed end and a free end, and is configured to move between a first position wherein the arm is retracted within the elongate body and the fixed end is located proximal to the free end in the first position, and a second position wherein the free end extends away from the elongate body, the free end rotating away from the elongate body when the arm moves from the first position to the second position, each arm comprising at least one suture mount at the free end;
a second plurality of arms proximal to the first plurality of arms, wherein each arm of the second plurality of arms is configured to move between a first position wherein the arm is retracted within the elongate body, and a second position wherein the arm has a free end extending away from the elongate body, each of the second plurality of arms having a length extending from an end coupled to the elongate body to the free end, and a width that is transverse to the length;
a sheath adapted to surround at least a portion of the elongate body;
a plurality of needles, each needle configured to move between a retracted position in which a distal point of the needle is proximal to the second plurality of arms and a deployed position in which the distal point of the needle extends through an arm of the second plurality of arms and into a corresponding suture mount of the first plurality of arms, wherein each of the second plurality of arms comprises a needle guide path that extends across the width of each of the second plurality of arms; and
a plurality of suture portions, wherein each suture portion has a suture end releasably retained within the suture mount of a corresponding arm of the first plurality of arms.

22. The suturing system of claim 21, wherein the first plurality of arms comprises four arms near the distal end.

23. The suturing system of claim 22, wherein the suturing device comprises four needles, each needle associated with a corresponding arm of the first plurality of arms.

24. The suturing system of claim 22, wherein the second plurality of arms comprises four arms, each of the second plurality of arms aligned with a corresponding arm of the first plurality of arms.

25. The suturing system of claim 21, wherein the needles are configured to simultaneously move to the deployed position.

26. The suturing system of claim 21, wherein the free ends of the each of the first plurality of arms move proximally when the arms move from the first position to the second position.

* * * * *